US012582512B2

(12) United States Patent 
Myung et al.

(10) Patent No.: US 12,582,512 B2 
(45) Date of Patent: Mar. 24, 2026

(54) METHOD FOR FORMING PTFE COATING FILM ON STENT, AND STENT MANUFACTURED THEREBY

(71) Applicant: BCM Co., Ltd., Gyeonggi-do (KR)

(72) Inventors: Byung Cheol Myung, Gyeonggi-do (KR); Houn Sung Kim, Gyeonggi-do (KR)

(73) Assignee: BCM CO., LTD., Gyeonggi-do (KR)

( * ) Notice: Subject to any disclaimer, the term of this patent is extended or adjusted under 35 U.S.C. 154(b) by 496 days.

(21) Appl. No.: 18/251,027

(22) PCT Filed: Oct. 27, 2021

(86) PCT No.: PCT/KR2021/015164 
§ 371 (c)(1), 
(2) Date: Apr. 28, 2023

(87) PCT Pub. No.: WO2022/108158 
PCT Pub. Date: May 27, 2022

(65) Prior Publication Data

US 2023/0372080 A1 Nov. 23, 2023

(30) Foreign Application Priority Data

Nov. 17, 2020 (KR) ........................ 10-2020-0153349

(51) Int. Cl. 
*A61F 2/07* (2013.01) 
*A61L 31/10* (2006.01)

(52) U.S. Cl. 
CPC ................ *A61F 2/07* (2013.01); *A61L 31/10* (2013.01); *A61F 2240/002* (2013.01); *A61L 2420/02* (2013.01)

(58) Field of Classification Search 
CPC ........ A61F 2/07; A61F 2/86; A61F 2240/002; A61F 2240/02; A61F 2240/00; A61F 2210/0076; A61F 2230/001; A61F 2250/0039; A61F 2002/072; A61L 31/10 
See application file for complete search history.

(56) References Cited

U.S. PATENT DOCUMENTS

| | | | |
|---|---|---|---|
| 6,790,225 B1 * | 9/2004 | Shannon | A61F 2/07 623/1.13 |
| 2005/0027347 A1 * | 2/2005 | Chobotov | B29C 66/836 623/1.13 |
| 2007/0173917 A1 * | 7/2007 | Hayashi | A61F 2/07 623/1.1 |
| 2019/0351099 A1 * | 11/2019 | McCarthy | A61L 27/48 |

* cited by examiner

*Primary Examiner* — Brooke Labranche 
(74) *Attorney, Agent, or Firm* — IP & T GROUP LLP

(57) ABSTRACT

The present invention relates to a method of forming a PTFE film on a stent, a stent manufactured thereby, and more particularly to a method capable of forming a PTFE film on a stent regardless of the shape of the stent, preventing the PTFE film from being peeled off from the stent, and facilitating formation of the PTFE film on the stent, a stent manufactured through the method.

36 Claims, 35 Drawing Sheets

METHOD FOR FORMING PTFE COATING FILM ON STENT, AND STENT MANUFACTURED THEREBY

CROSS-REFERENCE TO RELATED APPLICATION

This application is a national stage application of PCT/KR2021/015164 filed on Oct. 27, 2021, which claims priorities of Korean patent application number 10-2020-0153349 filed on Nov. 17, 2020. The disclosure of each of the foregoing applications is incorporated herein by reference in its entirety.

TECHNICAL FIELD

The present invention relates to a method of forming a PTFE film on a stent, and a stent manufactured thereby, and more particularly to a method capable of forming a PTFE film on a stent regardless of the shape of the stent, preventing the PTFE film from being peeled off from the stent, and facilitating formation of the PTFE film on the stent, and a stent manufactured through the method.

BACKGROUND ART

In general, when a lesion that is narrowed or occluded by a tumor or other reasons is generated in a lumen in the human body, such as the respiratory tract, esophagus, duodenum, biliary tract, or urethral canal, the lumen does not function normally. Hence, a stent is inserted into a lesion generated in a lumen in the human body to expand the lesion and thus to enable the lumen to function normally.

In addition, a film made of PTFE is formed on the stent.

In this regard, Patent Document 1 discloses a method of manufacturing a stent having an artificial blood vessel adhered thereto, the method including a process of manufacturing a stent having a hollow cylindrical body formed by intertwining hyper-elastic shape memory alloy wires, a process of preparing for adhesion by winding an artificial blood vessel (polytetrafluoroethylene (PTFE)) obliquely on an outer surface of a SUS rod to form an inner artificial blood vessel layer, placing the stent on the inner artificial blood vessel layer, winding an artificial blood vessel (polytetrafluoroethylene (PTFE)) obliquely on an outer surface of the stent to form an outer artificial blood vessel layer, and placing a silicon tube on the outer artificial blood vessel layer, and a process of integrally adhering the inner and outer artificial blood vessel layers to the stent by fixedly mounting the SUS rod in a vacuum heating device, executing vacuum operation so that the inner and outer artificial blood vessel layers located on the inner and outer surfaces of the stent are adsorbed to the stent while wrapping the inner and outer surfaces of the stent, and executing heating operation so that the inner and outer artificial blood vessel layers are fused to each other by heat and integrally adhered to the stent.

However, in the case of Patent Document 1, when the stent having an expanded portion having a relatively large diameter is placed on the SUS rod, a gap is formed between the SUS rod and the expanded portion, and thus it is not possible to wind the outer artificial blood vessel made of PTFE.

That is, it is not possible to form the outer artificial blood vessel layer made of PTFE on the expanded portion of the stent, which causes inconvenience of having to coat silicone or the like on the expanded portion later.

In the conventional art, as shown in FIG. 1, inner and outer films 3a and 3b, which are made of PTFE and wrap a stent 3, are heated by a heating rod 2 fitted into a jig 1, and the stent 3, with the jig 1 fitted thereinto, is pressed so that the inner and outer films 3a and 3b made of PTFE are adhered to each other, whereby a plurality of spaces 3c defined in the stent 3 is sealed.

However, in many cases, the stent 3, with the jig 1 fitted thereinto, is not properly pressed, and thus portions of the inner and outer films 3a and 3b made of PTFE are not adhered to each other.

That is, there is a concern that the inner and outer films 3a and 3b will be peeled off from the stent 3.

In addition, in the conventional art, as shown in FIG. 2, one of the inner and outer films 3a and 3b made of PTFE is connected to the stent 3 by stitching a suture thread 3d through the spaces 3c. However, it is difficult to stitch the suture thread 3d to connect the above elements.

RELATED ART DOCUMENT

Patent Document

Patent Document 1: Korean Patent Laid-Open Publication No. 10-2015-0052719 (published on May 14, 2015)

DISCLOSURE

Technical Problem

It is an object of the present invention to provide a method capable of forming a PTFE film on a stent regardless of the shape of the stent, preventing the PTFE film from being peeled off from the stent, and facilitating formation of the PTFE film on the stent, and a stent manufactured through the method.

Technical Solution

In order to accomplish the above object, the present invention provides a method of forming a PTFE film on a stent using a jig being manufactured in a same shape as a stent having a plurality of spaces and a stent manufactured through the method of forming a PTFE film on a stent, the method including performing a taping process of winding a first sheet of PTFE tape on an entire outer surface of the jig, fitting the jig into a stent, performing a taping process of winding a second sheet of PTFE tape on an entire outer surface of the stent, putting the stent, with the jig fitted thereinto, into an oven to heat the jig and the stent so that the first and second sheets of PTFE tape become ready to be adhered to each other, taking the jig and the stent out of the oven, fitting the heated jig and the heated stent, with the first and second sheets of PTFE tape respectively wound thereon, into a first receiving portion of a lower elastic member, which is formed in the same shape as a portion of the jig, and a first receiving portion of an upper elastic member, which is formed in the same shape as the remaining portion of the jig, fitting the lower elastic member and the upper elastic member into a first receiving portion of a mold, which is formed in the same shape as the lower elastic member and the upper elastic member, pressing the upper elastic member using a press member to transmit pressure from the mold and the press member to entire areas of the lower elastic member and the upper elastic member so that the first and second sheets of PTFE tape are adhered to each other to form a PTFE film on the stent and the PTFE film fills a plurality of spaces, taking the lower elastic member and the upper elastic member out of the first receiving portion of the mold, with pressure transmitted from the press member released, taking the stent out of the first receiving portion of the lower elastic member and the first receiving portion of the upper elastic member, and removing the jig from the stent.

Advantageous Effects

According to the present invention, since a jig is manufactured in the same shape as a stent, the jig is brought into close contact with an inner surface of the stent regardless of the shape of the stent.

That is, it is possible to stably wind a second sheet of PTFE tape on an outer surface of the stent supported by the jig regardless of the shape of the stent.

In other words, it is possible to easily form a PTFE film regardless of the shape of the stent, unlike the conventional art.

According to the present invention, it is possible to cause first and second sheets of PTFE tape to be adhered to each other by uniformly pressing upper and lower elastic members using a mold and a press member.

That is, since the first and second sheets of PTFE tape are more evenly adhered to each other than in the conventional art to fill spaces in the stent, a PTFE film is stably formed on the stent.

In other words, it is possible to more reliably prevent the PTFE film from being peeled off from the stent than in the conventional art.

According to the present invention, since the upper and lower elastic members are made of silicone or rubber, it is simple to manufacture the upper and lower elastic members.

According to the present invention, the PTFE film is formed on the stent by causing the first and second sheets of PTFE tape to be adhered to each other without using a conventional suture thread.

That is, it is possible to more easily form the PTFE film on the stent than in the conventional art.

According to the present invention, it is possible to move the press member upwards and downwards using a cylinder configured to be operated by hydraulic pressure or pneumatic pressure.

According to the present invention, since the jig or each of the upper and lower elastic members has a knob, it is possible to easily place or remove the stent into or from the upper and lower elastic members and the mold.

According to the present invention, in the case in which the first sheet of PTFE tape wound on the entire outer surface of the jig and the second sheet of PTFE tape wound on the entire outer surface of the stent are adhered to each other, the first and second sheets of PTFE tape prevent a lumen in a human body and a lesion from being inserted into spaces in the stent.

In addition, in the case in which the first sheets of PTFE tape wound on two opposite sides of the outer surface of the jig and the second sheet of PTFE tape wound on the entire outer surface of the stent are adhered to each other, the second sheet of PTFE tape located outside the stent prevents a lumen in a human body and a lesion from being inserted into spaces in the stent.

In addition, in the case in which the first sheet of PTFE tape wound on the entire outer surface of the jig and the second sheets of PTFE tape wound on two opposite sides of the outer surface of the stent are adhered to each other, the first sheet of PTFE tape located inside the stent prevents a lumen in a human body and a lesion inserted into spaces from protruding to the interior of the stent.

In addition, in the case in which the plurality of first sheets of PTFE tape wound at predetermined intervals on the outer surface of the jig and the second sheet of PTFE tape wound on the entire outer surface of the stent are adhered to each other, sections in each of which both the first and second sheets of PTFE tape are formed and sections in each of which only the second sheet of PTFE tape is formed are separately formed in the longitudinal direction of the stent.

That is, a lumen in a human body and a lesion are prevented from being inserted into spaces in the stent in the sections in each of which both the first and second sheets of PTFE tape are formed and the sections in each of which only the second sheet of PTFE tape is formed.

In addition, in the case in which the first PTFE tape wound on the entire outer surface of the jig and the plurality of second sheets of PTFE tape wound at predetermined intervals on the outer surface of the stent are adhered to each other, sections in each of which both the first and second sheets of PTFE tape are formed and sections in each of which only the first sheet of PTFE tape is formed are separately formed in the longitudinal direction of the stent.

That is, a lumen in a human body and a lesion are prevented from being inserted into spaces in the stent in the sections in each of which both the first and second sheets of PTFE tape are formed, and a lumen in a human body and a lesion inserted into the spaces are prevented from protruding to the interior of the stent in the sections in each of which only the first sheet of PTFE tape is formed.

In addition, in the case in which the plurality of first sheets of PTFE tape and the plurality of second sheets of PTFE tape respectively wound at predetermined intervals on the outer surfaces of the jig and the stent are adhered to each other, sections in each of which both the first and second sheets of PTFE tape are formed and sections in each of which neither the first nor second sheet of PTFE tape is formed are separately formed in the longitudinal direction of the stent.

That is, a lumen in a human body and a lesion are prevented from being inserted into spaces in the stent in the sections in each of which both the first and second sheets of PTFE tape are formed, and a lumen in a human body and a lesion are inserted into the spaces in the sections in each of which neither the first nor second sheet of PTFE tape is formed, whereby the stent catches in the lumen in the human body and the lesion.

In addition, the degree of elasticity of the stent varies depending on the shape of the PTFE film formed on the stent.

As a result, the structure in which the stent catches in a lumen in a human body so as not to slip in a lesion varies depending on the shape of the PTFE film formed on the stent.

DESCRIPTION OF DRAWINGS

FIGS. 3 to 5 and 14 to 22 are views showing processes of manufacturing a stent having a PTFE film formed thereon according to a second embodiment of the present invention.

FIGS. 3 to 5 and 23 to 31 are views showing processes of manufacturing a stent having a PTFE film formed thereon according to a third embodiment of the present invention.

FIGS. 3 to 5 and 32 to 40 are views showing processes of manufacturing a stent having a PTFE film formed thereon according to a fourth embodiment of the present invention.

FIGS. 3 to 5 and 41 to 49 are views showing processes of manufacturing a stent having a PTFE film formed thereon according to a fifth embodiment of the present invention.

FIGS. 3 to 5 and 50 to 58 are views showing processes of manufacturing a stent having a PTFE film formed thereon according to a sixth embodiment of the present invention.

BEST MODE

Figure 1:
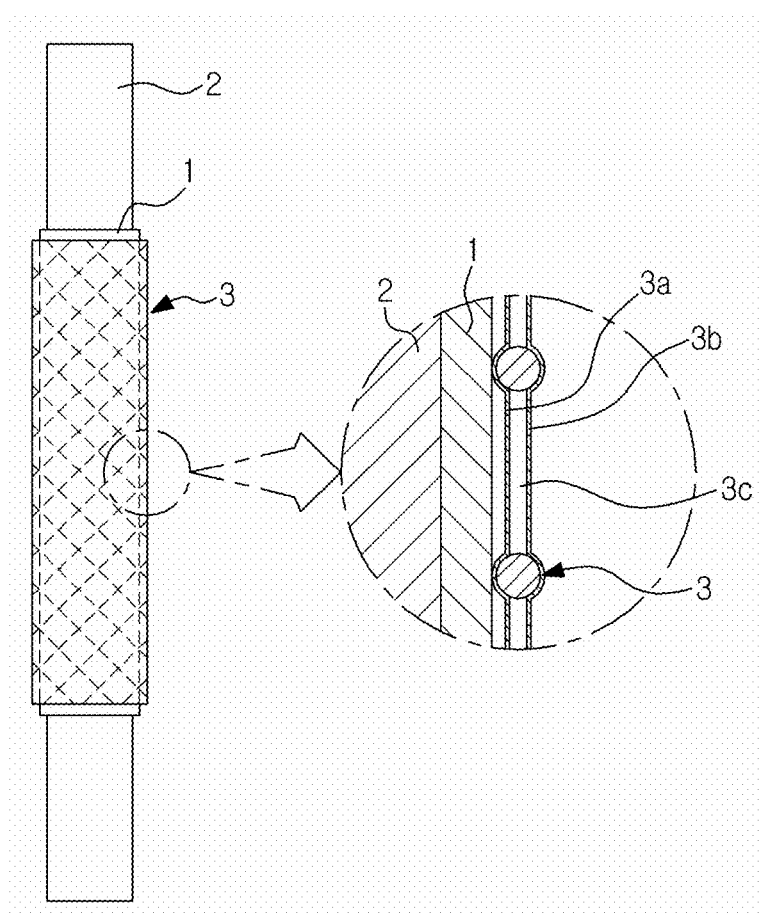
FIGS. 1 and 2 are use state views showing conventional methods of forming a PTFE film on a stent.
Figure 2:
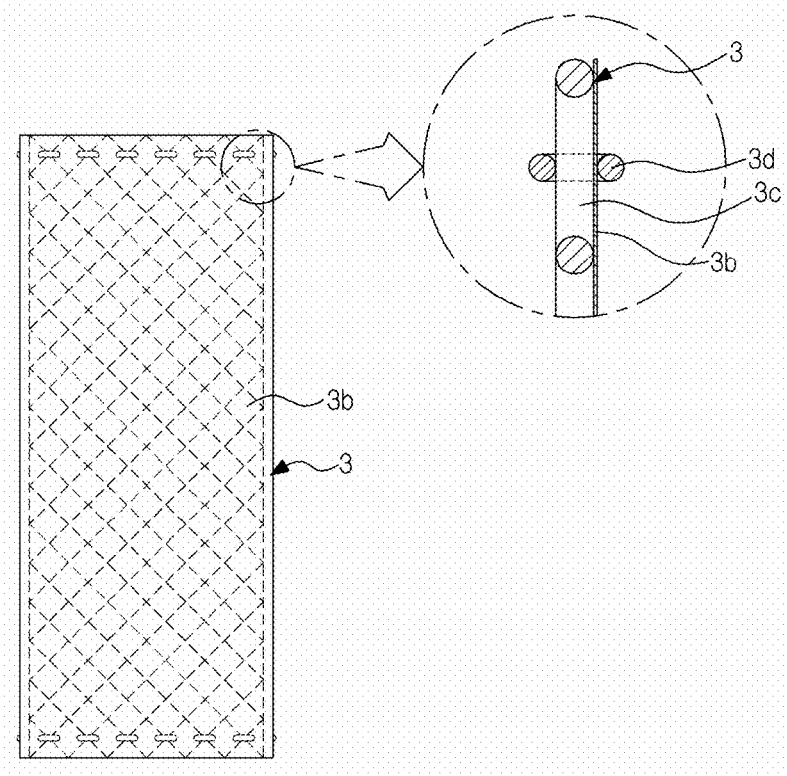
Figure 3:
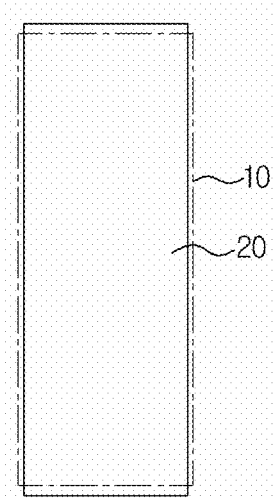
FIGS. 3 to 5 are front views showing jigs manufactured in the same shapes as various types of stents according to various embodiments of the present invention.
Figure 4:
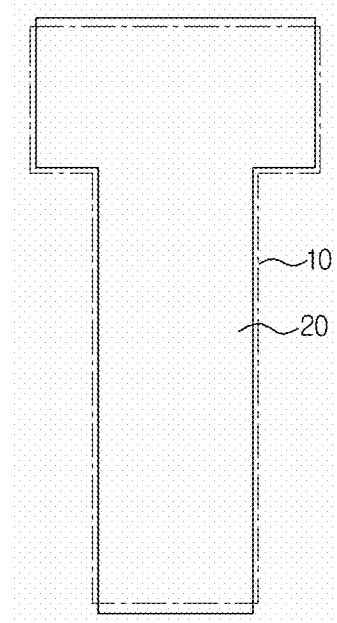
Figure 5:
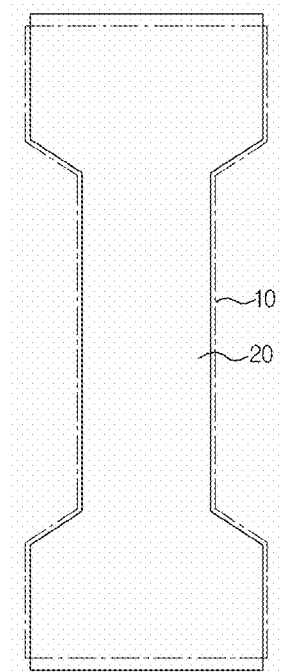
Figure 6:
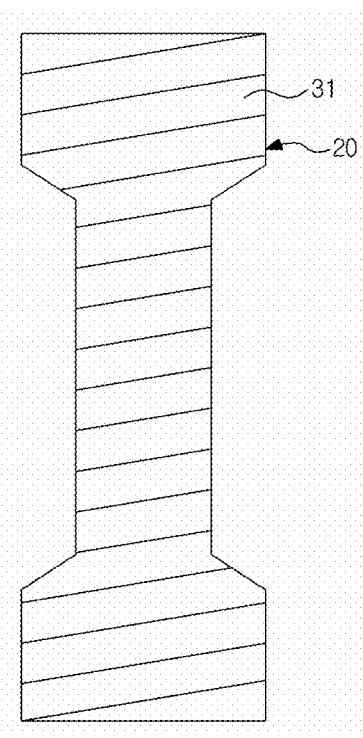
FIGS. 6 to 13 are views showing processes of manufacturing a stent having a PTFE film formed thereon according to a first embodiment of the present invention.
Figure 7:
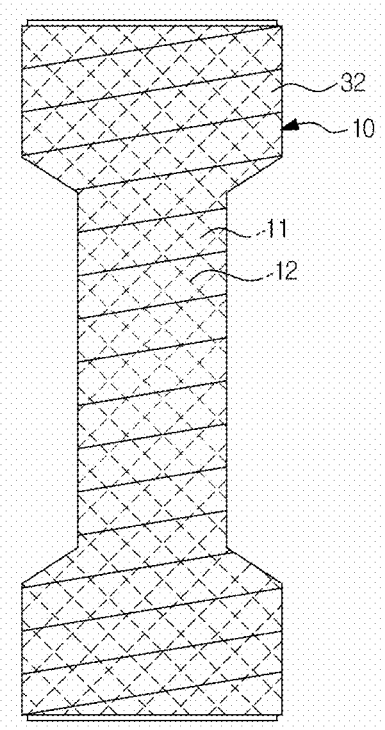
Figure 8:
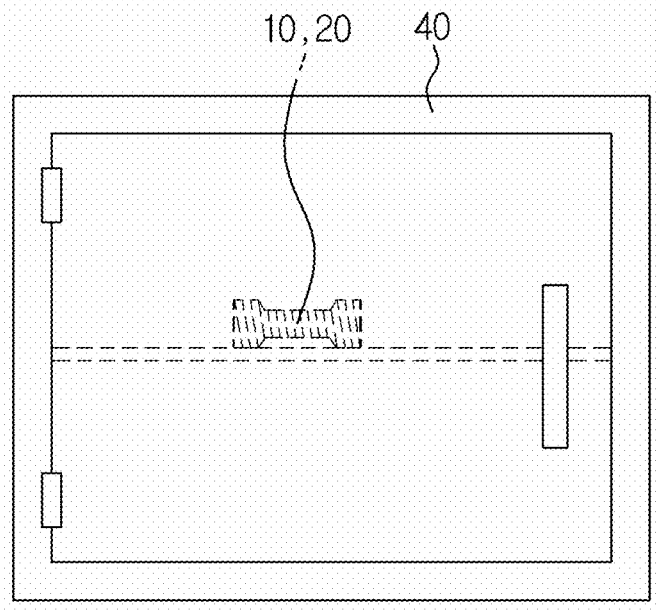
Figure 9:
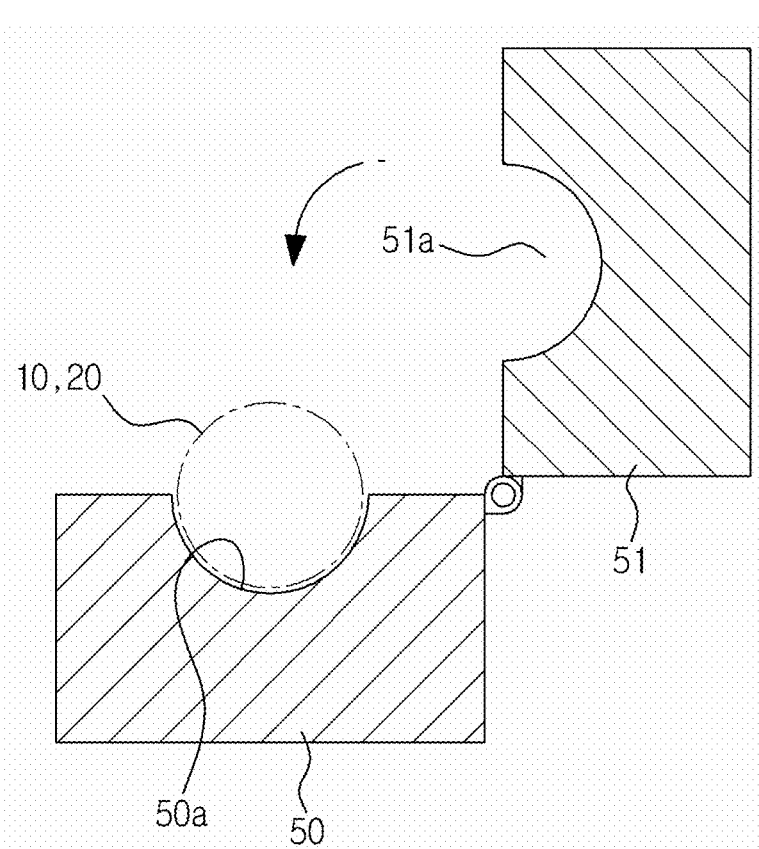
Figure 10:
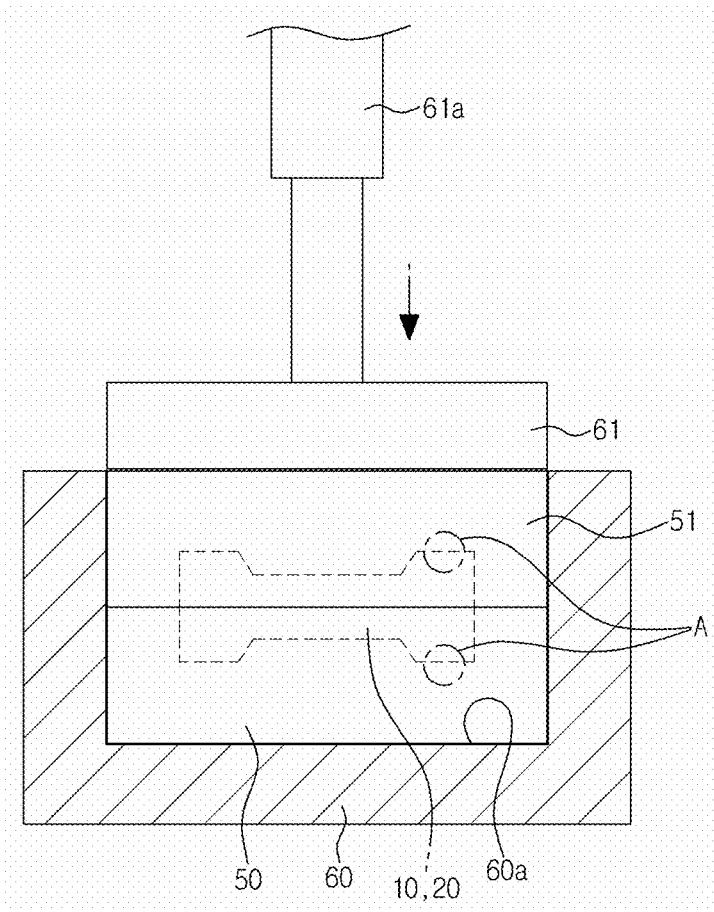
Figure 11:
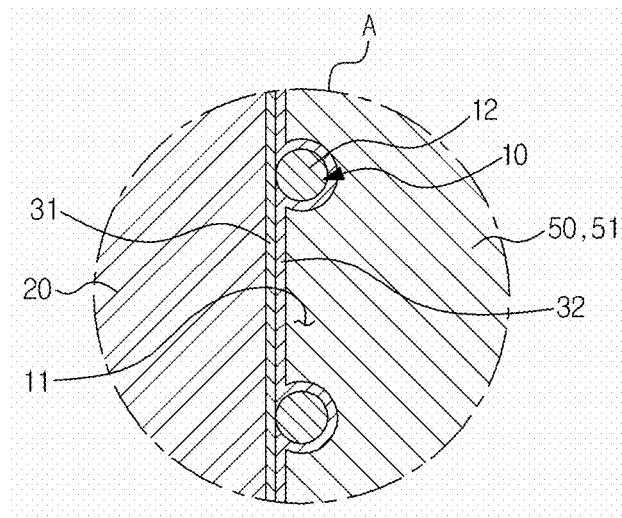
Figure 12:
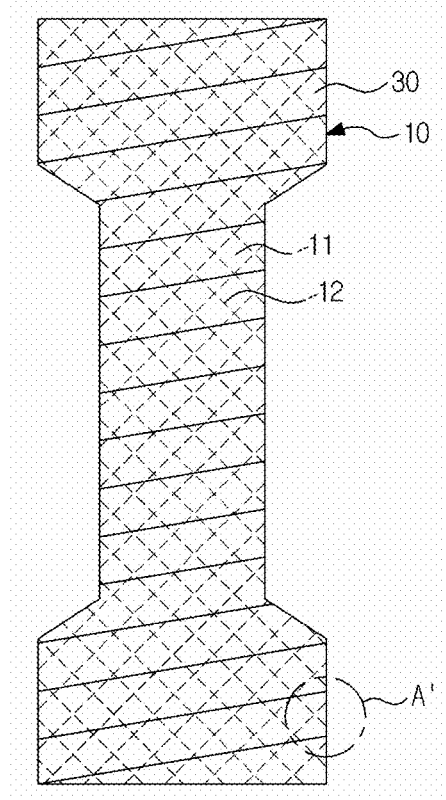
Figure 13:
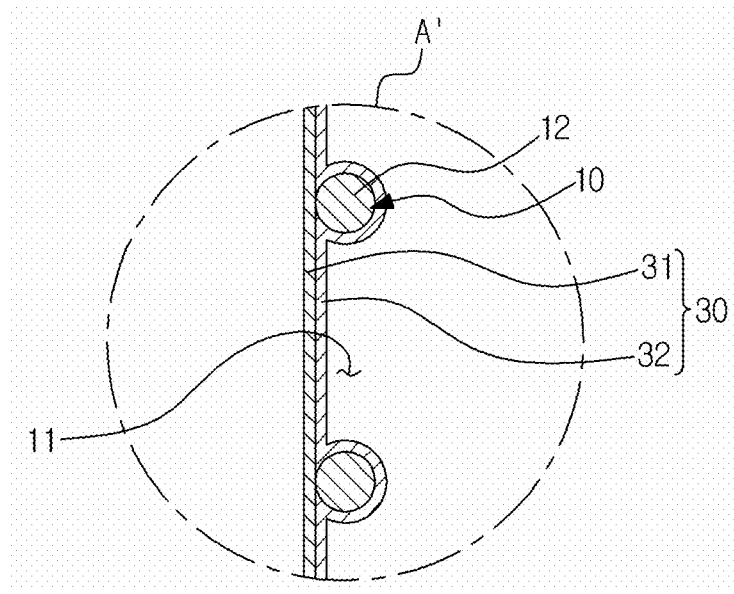
Figure 14:
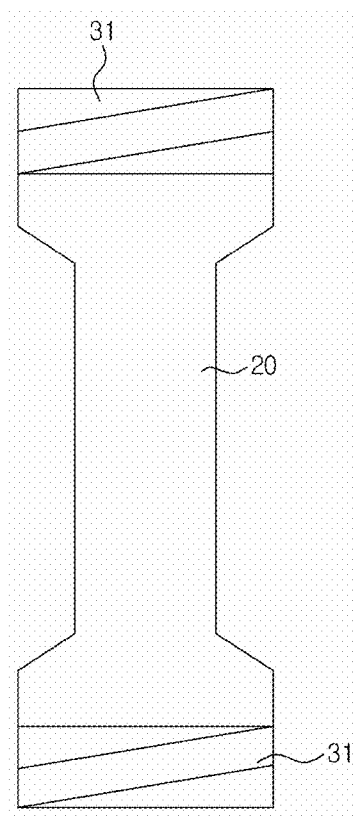
Figure 15:
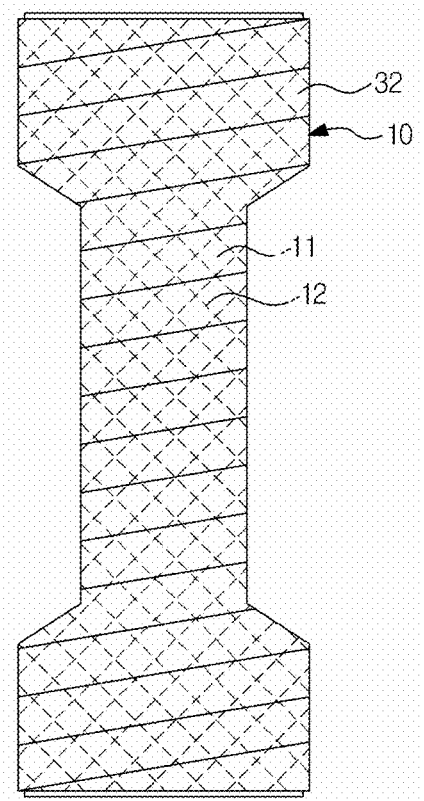
Figure 16:
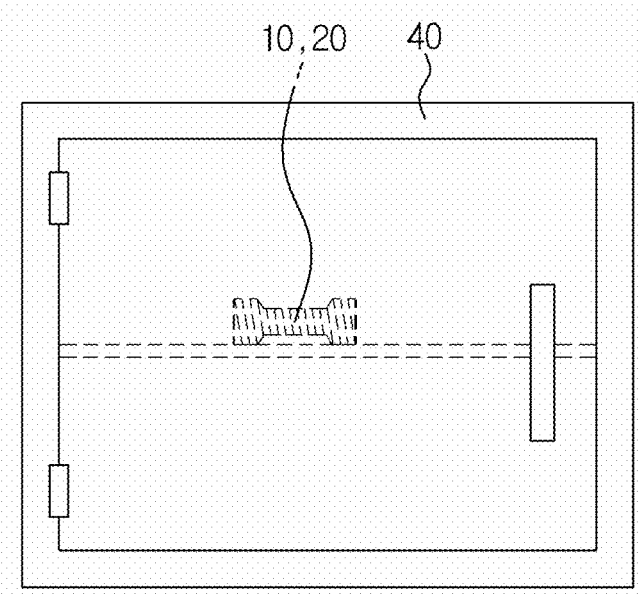
Figure 17:
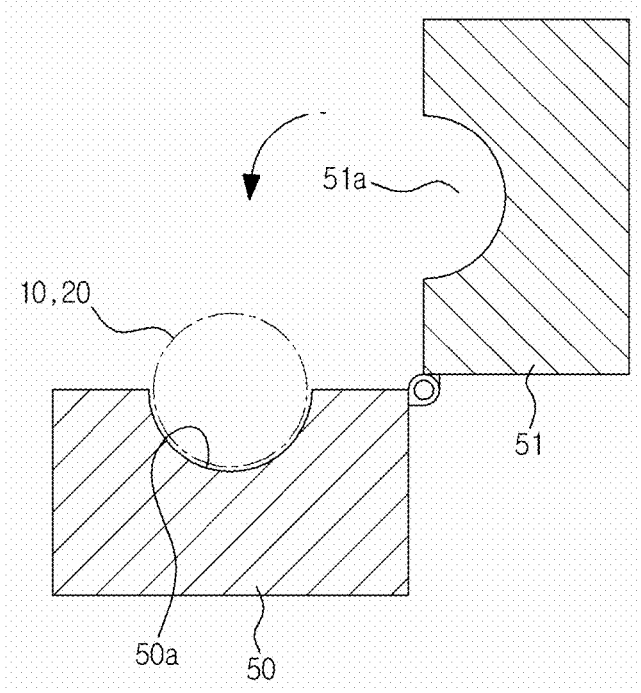
Figure 18:
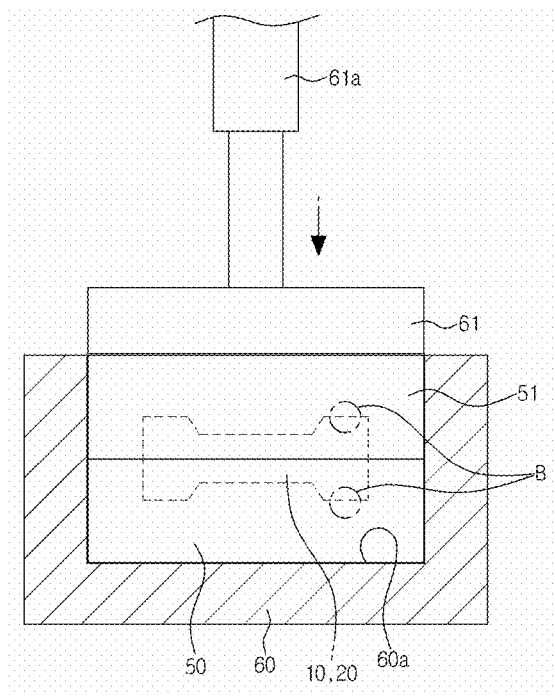
Figure 19:
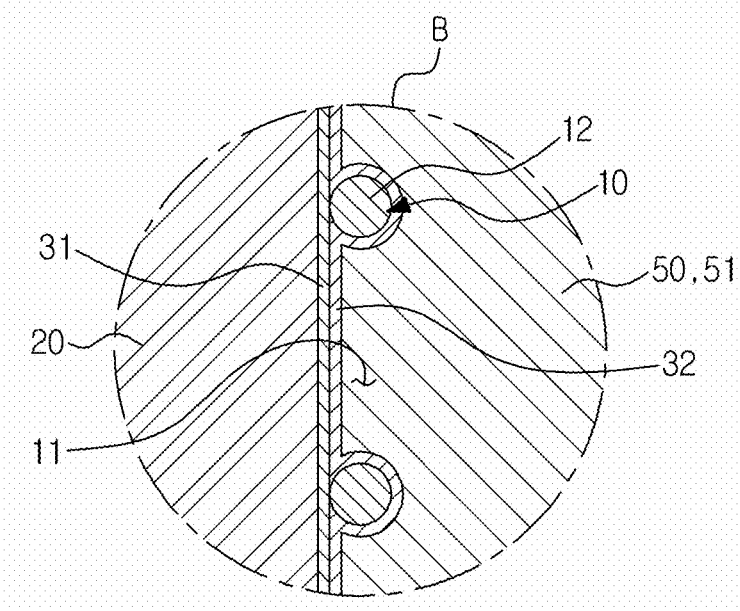
Figure 20:
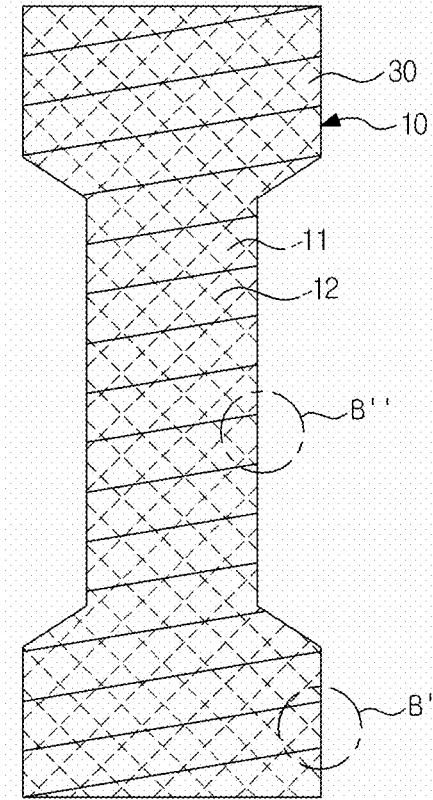
Figure 21:
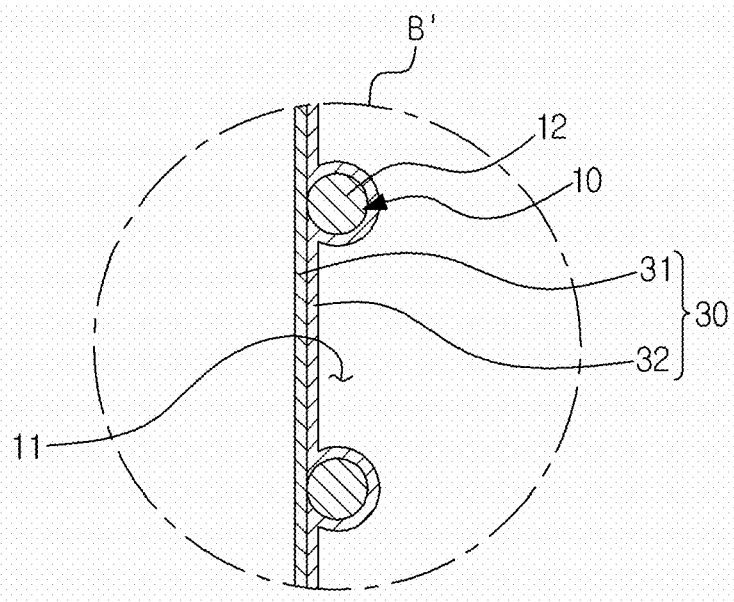
Figure 22:
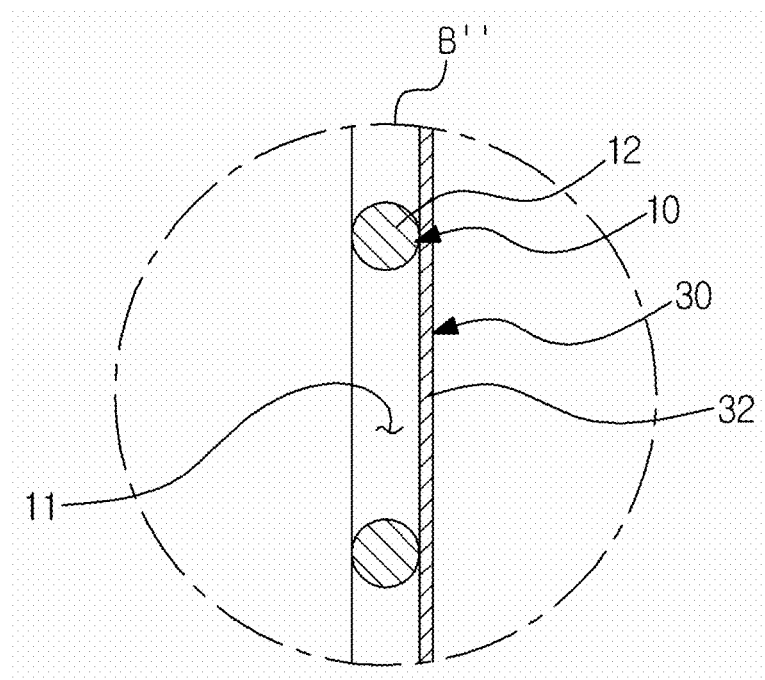
Figure 23:
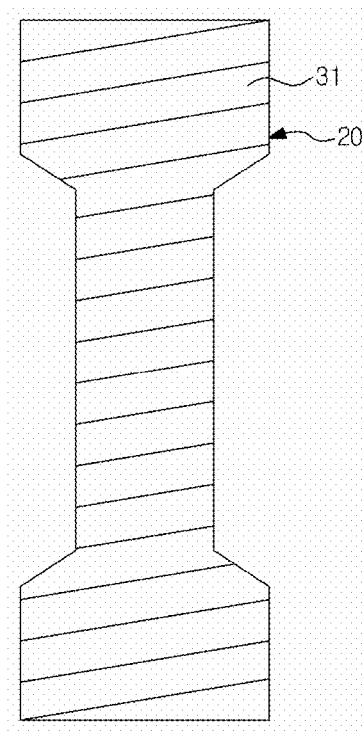
Figure 24:
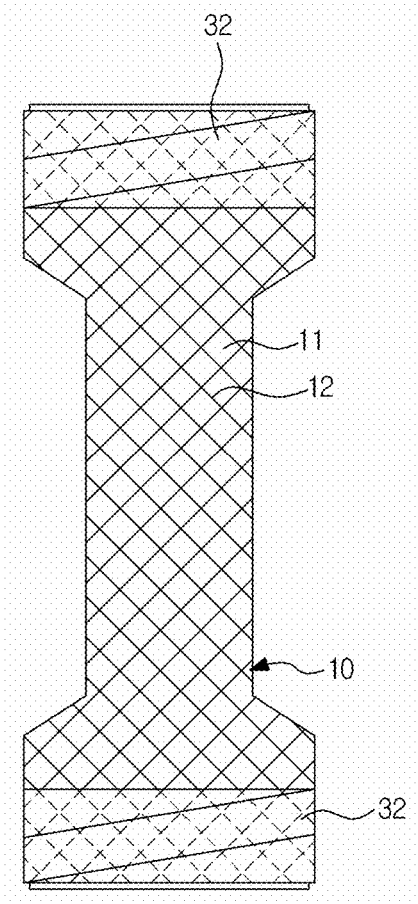
Figure 25:
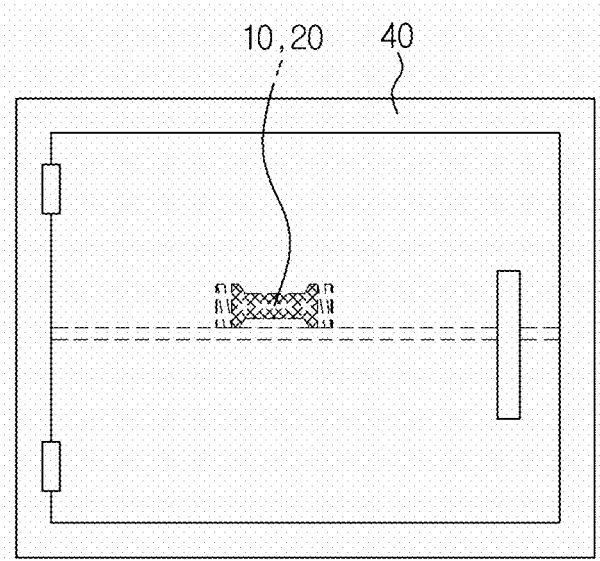
Figure 26:
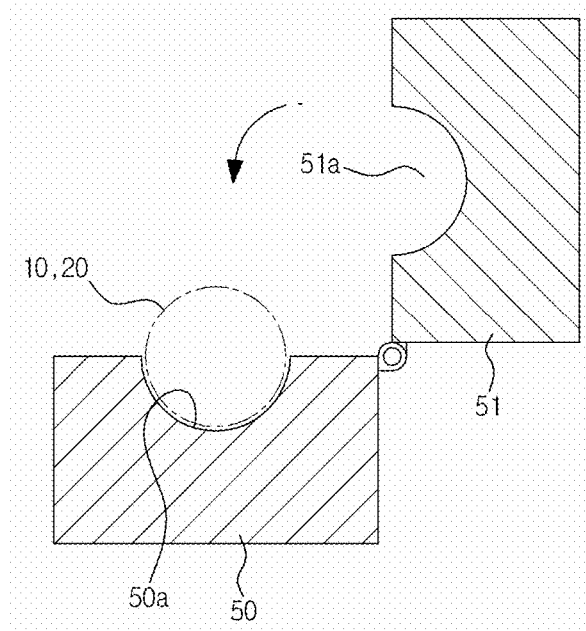
Figure 27:
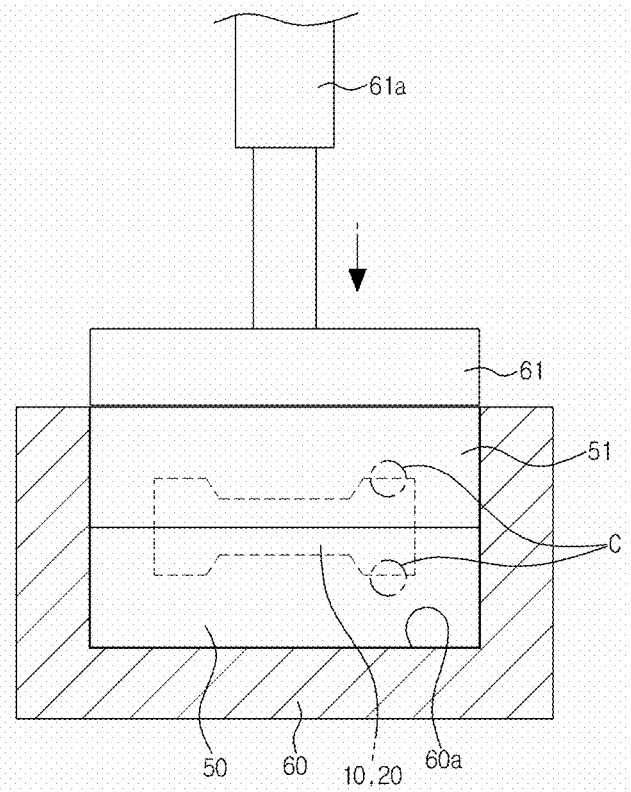
Figure 28:
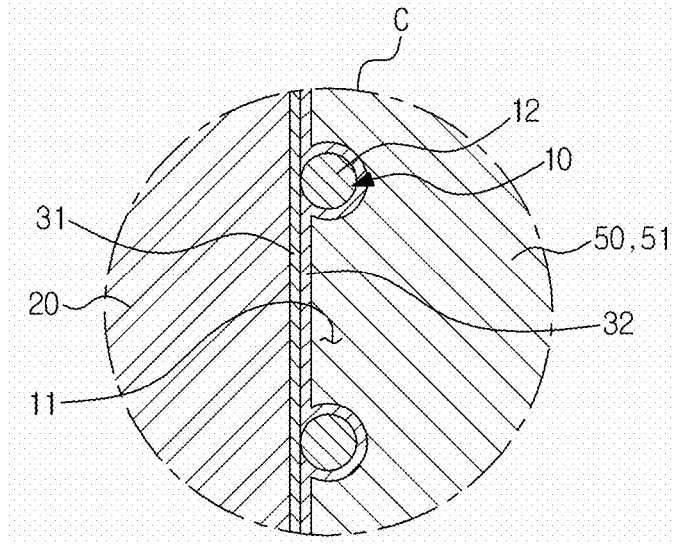
Figure 29:
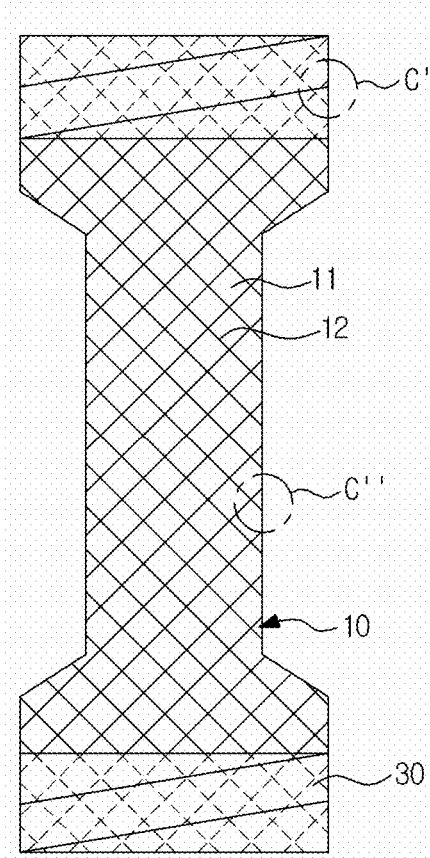
Figure 30:
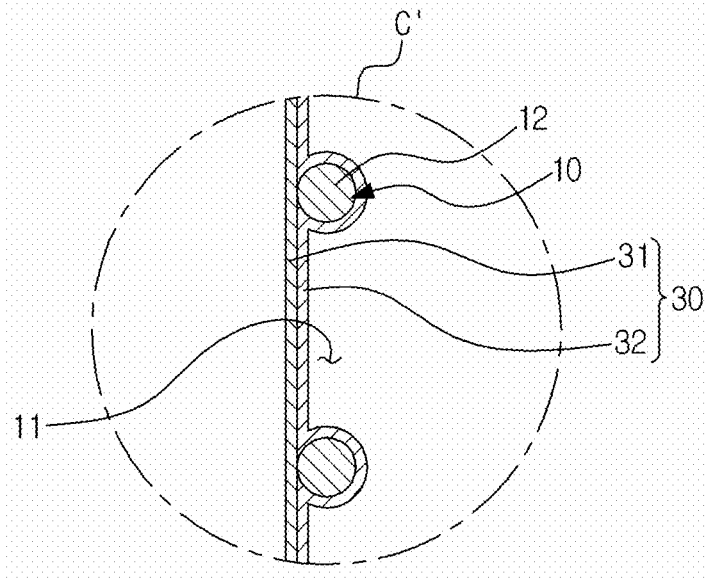
Figure 31:
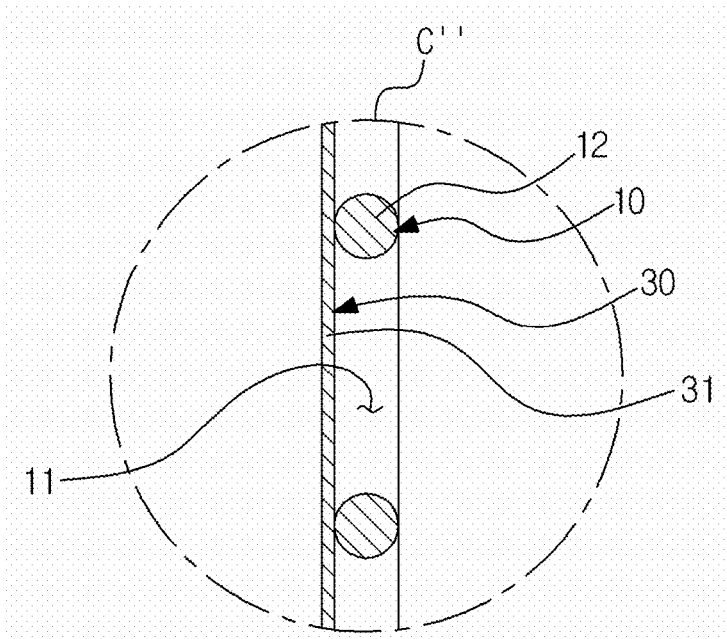
Figure 32:
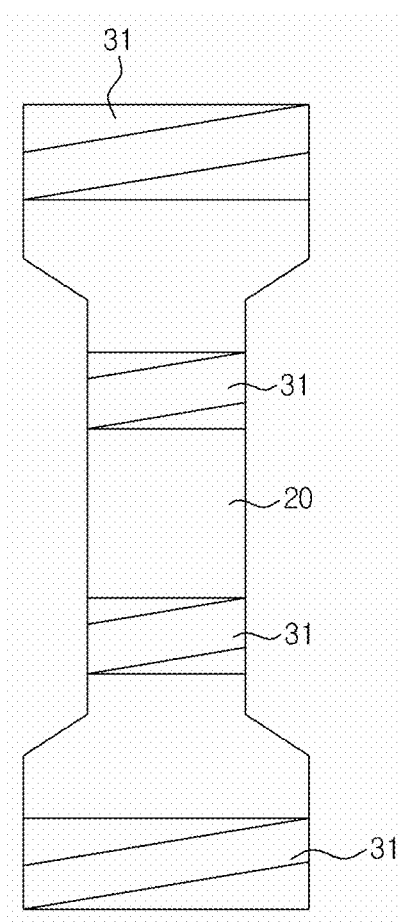
Figure 33:
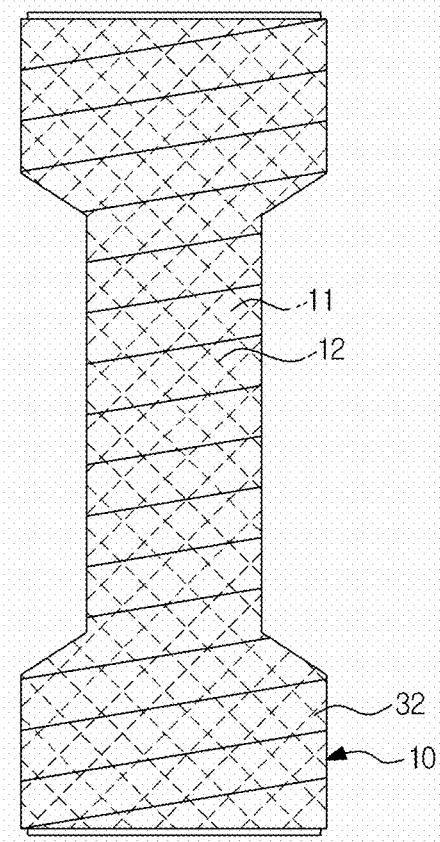
Figure 34:
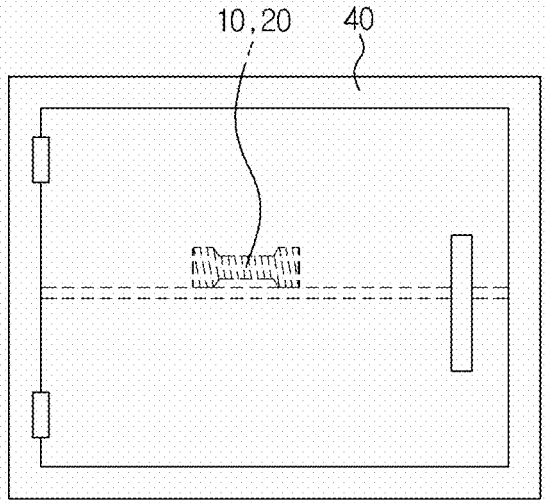
Figure 35:
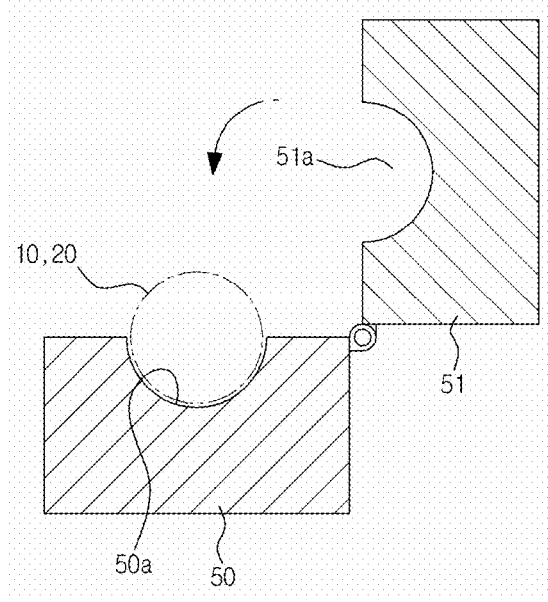
Figure 36:
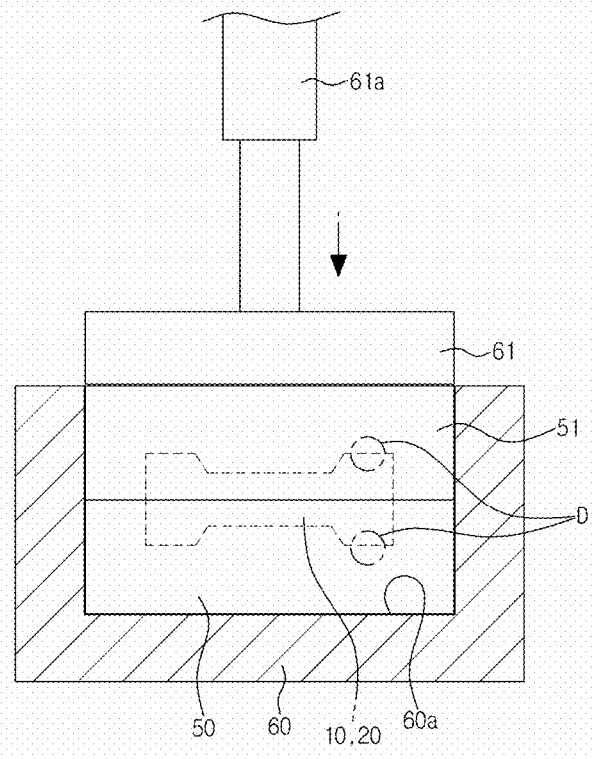
Figure 37:
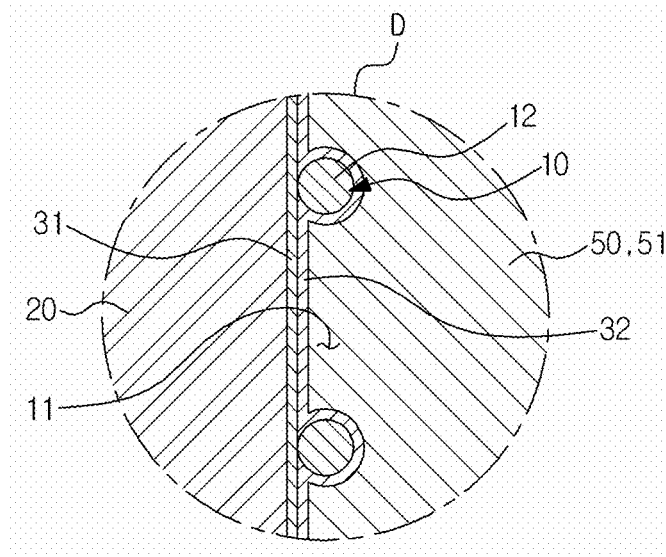
Figure 38:
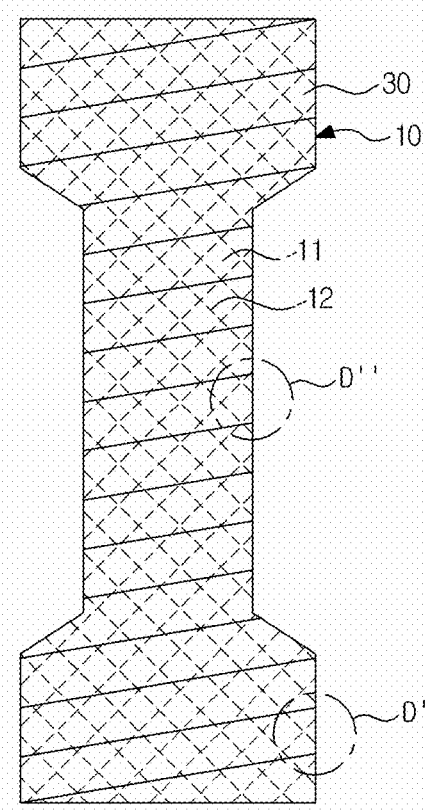
Figure 39:
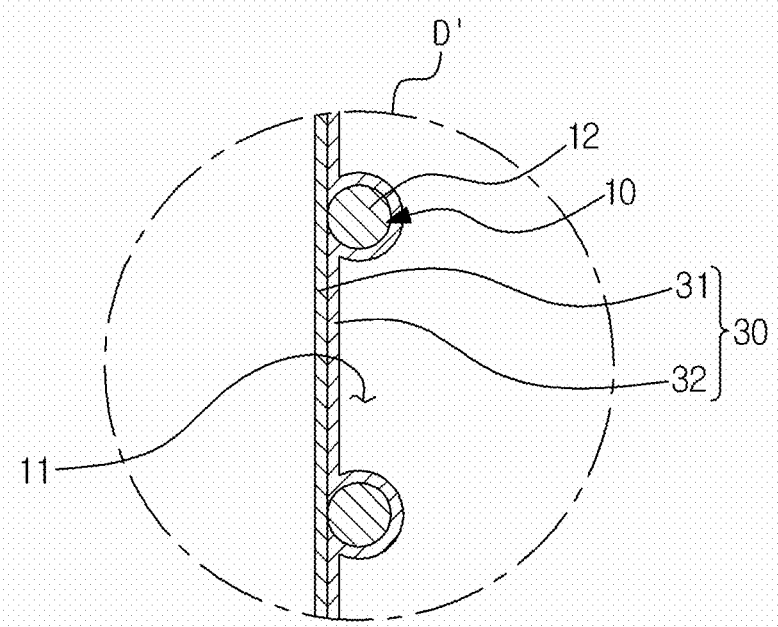
Figure 40:
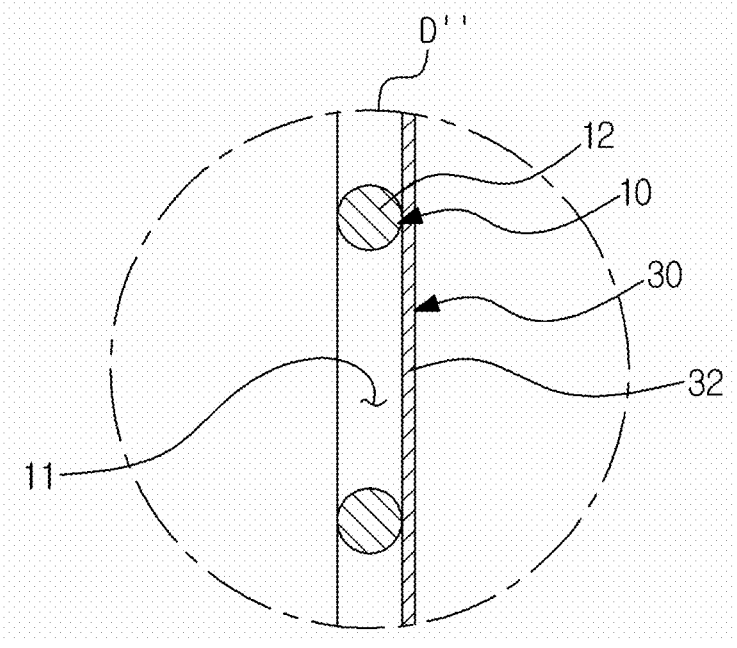
Figure 41:
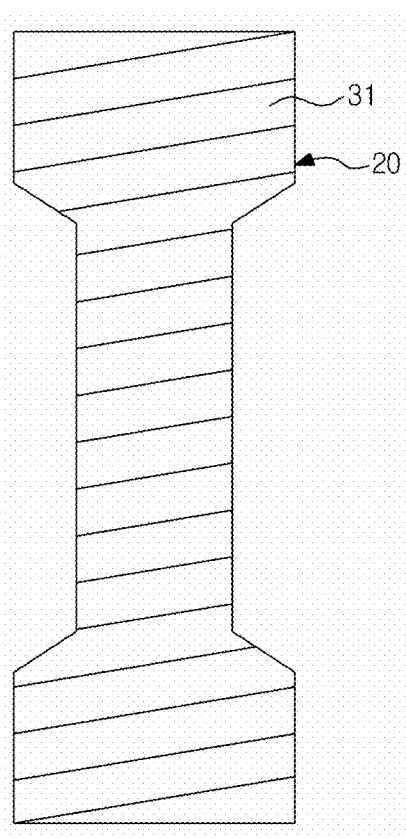
Figure 42:
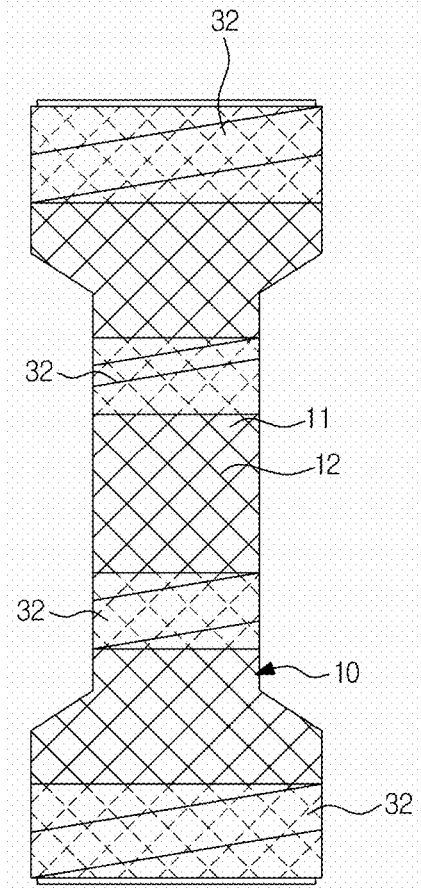
Figure 43:
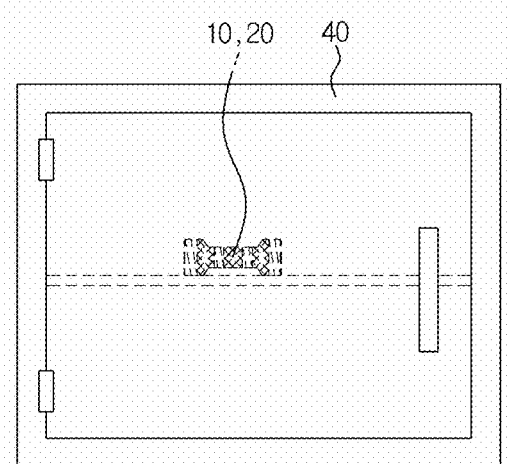
Figure 44:
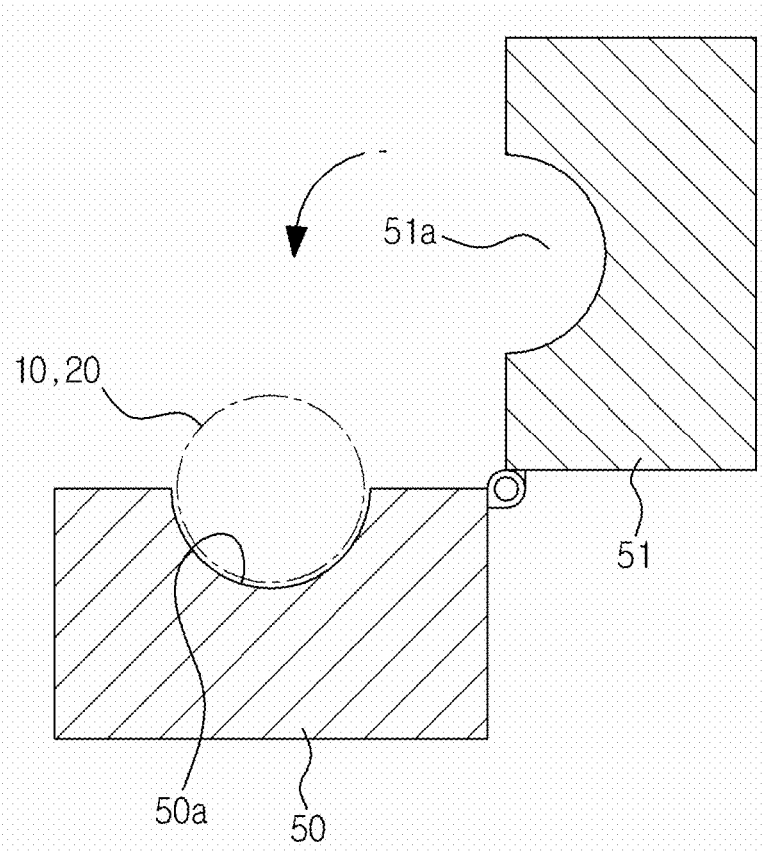
Figure 45:
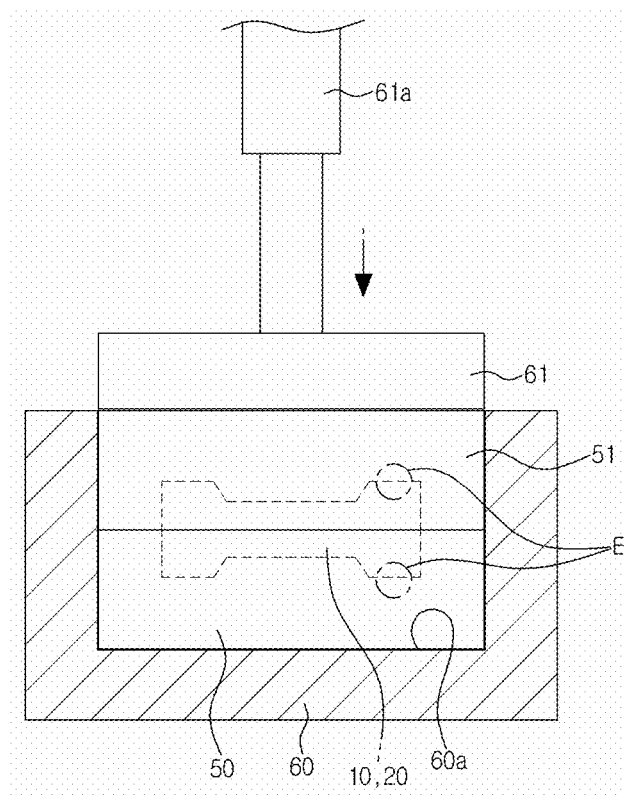
Figure 46:
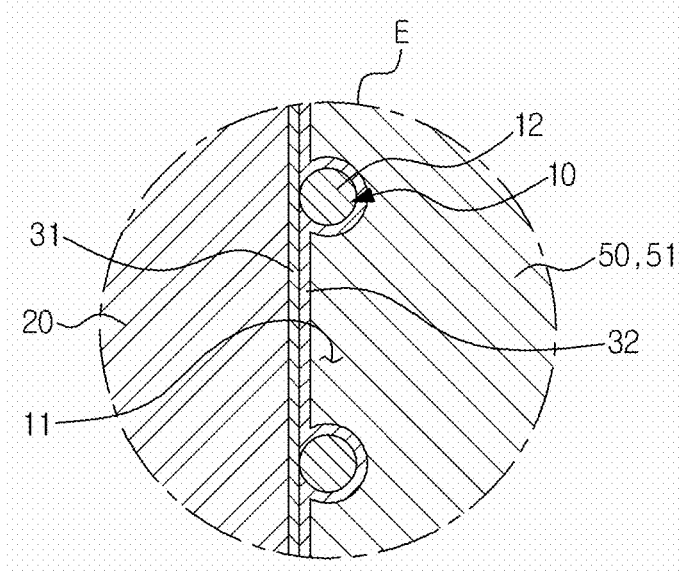
Figure 47:
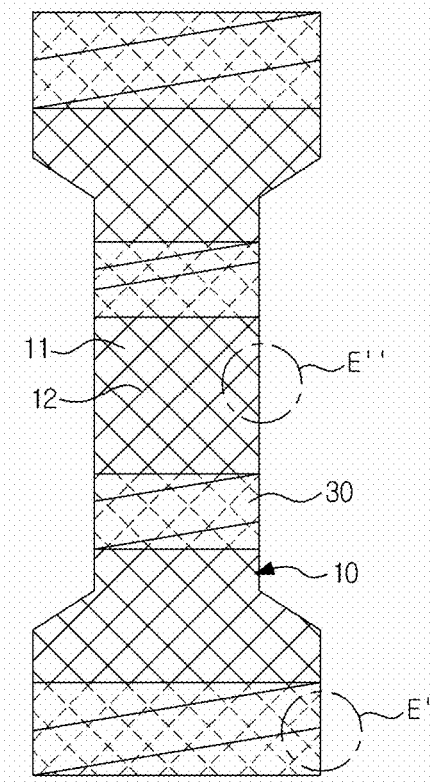
Figure 48:
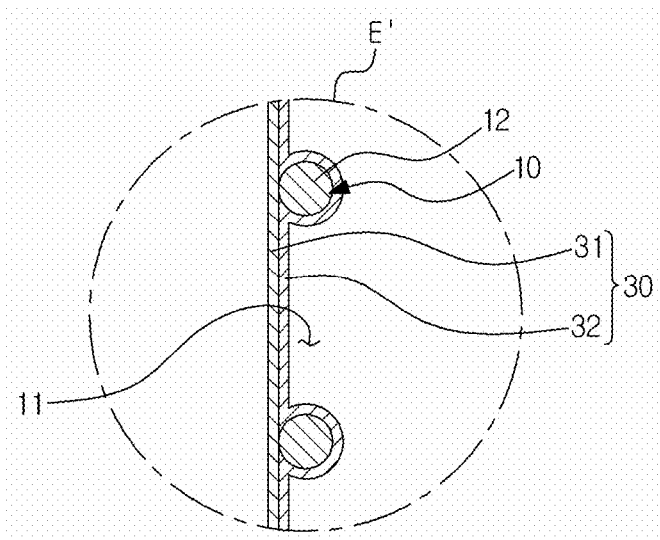
Figure 49:
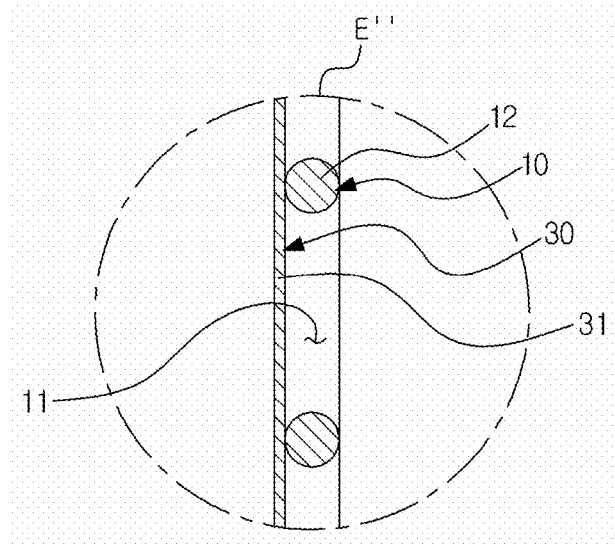
Figure 50:
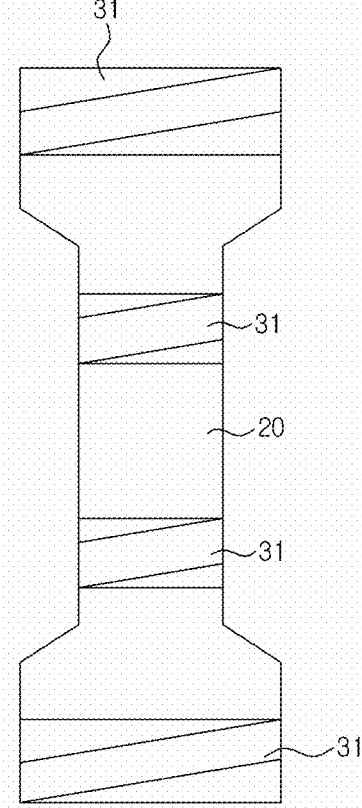
Figure 51:
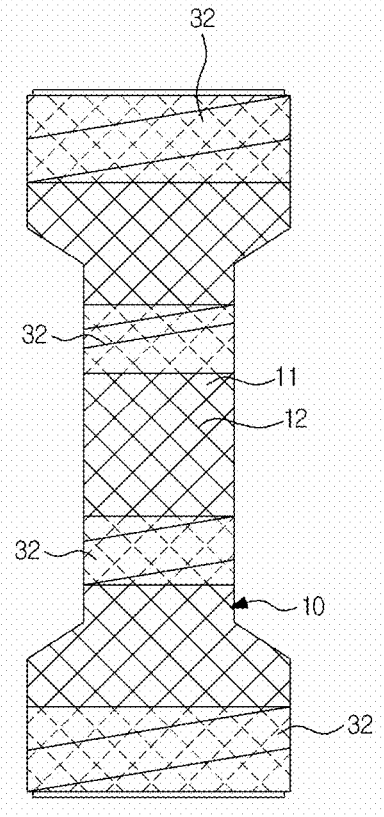
Figure 52:
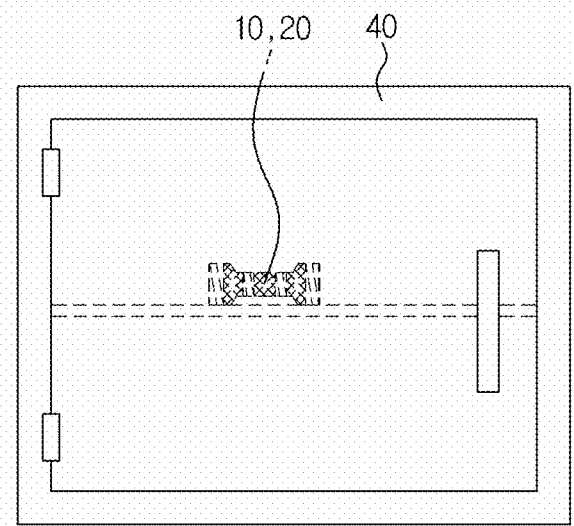
Figure 53:
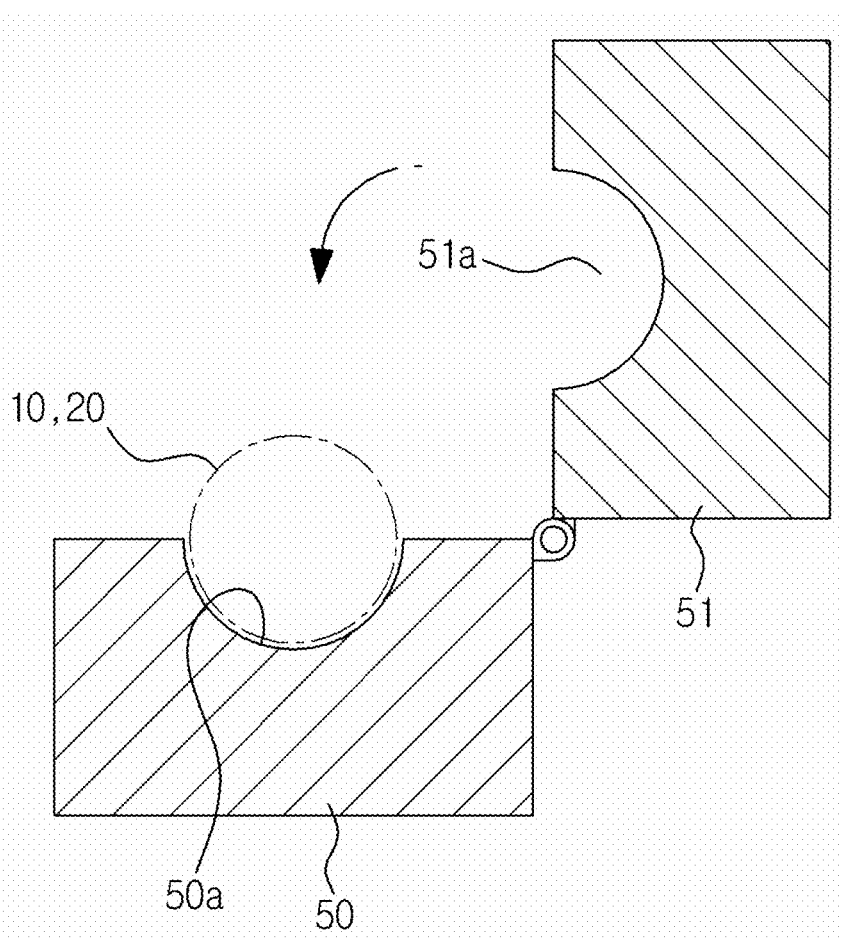
Figure 54:
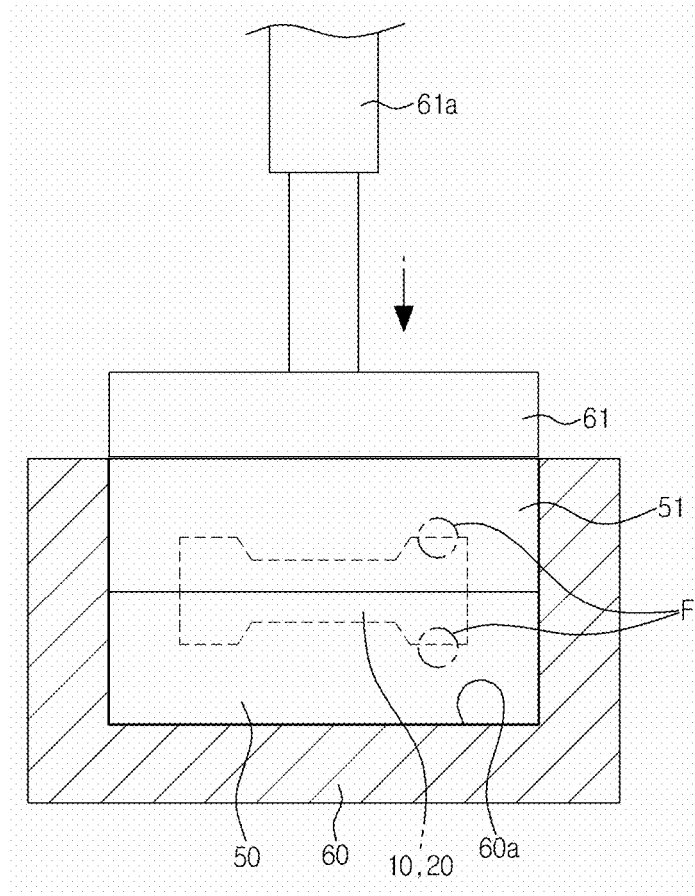
Figure 55:
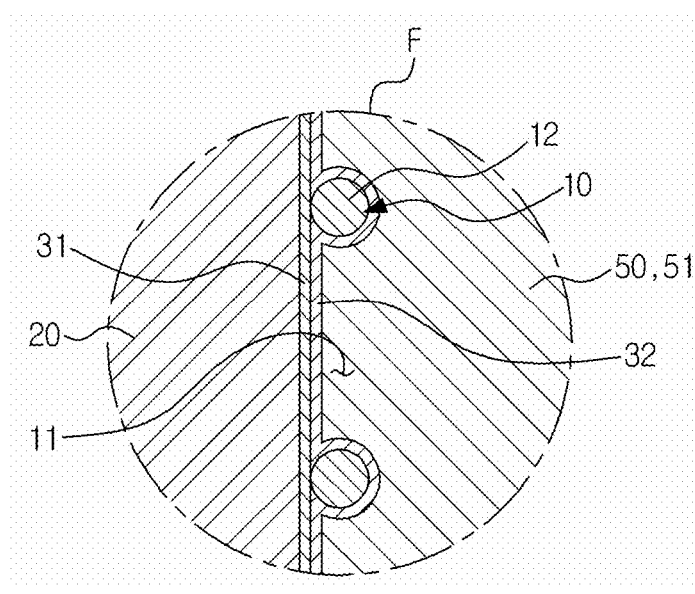
Figure 56:
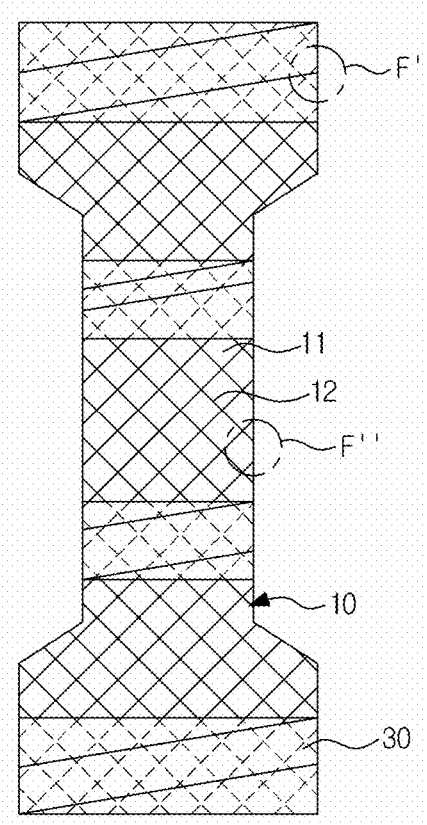
Figure 57:
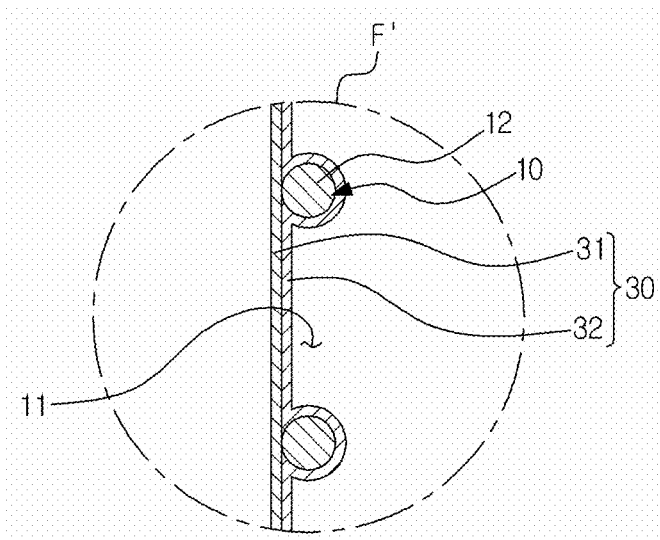
Figure 58:
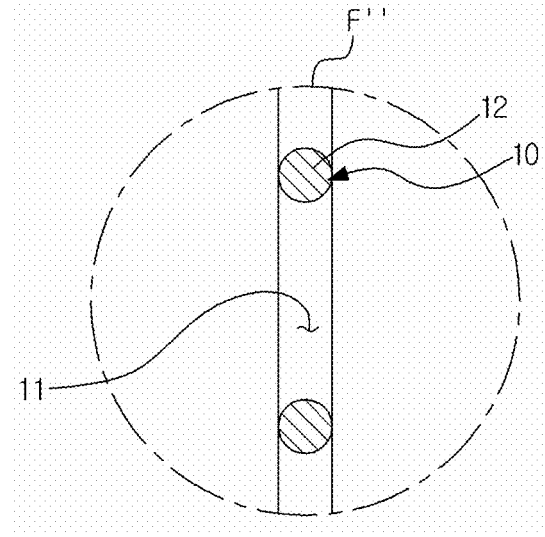

Hereinafter, various exemplary embodiments of the present invention will be described in detail with reference to the accompanying drawings.

As shown in FIGS. 3 to 13, a method of manufacturing a stent 10 according to a first embodiment of the present invention, on which a PTFE film 30 is formed, includes a process of preparing a jig 20 manufactured in the same shape as the stent 10 and a taping process of winding a first sheet of polytetrafluoroethylene (PTFE) tape 31 on the entire outer surface of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheet of PTFE tape 31 is wound on the jig 20 only in the spiral direction of the jig 20, only in the circumferential direction of the jig 20, or in a combination of the spiral and circumferential directions of the jig 20.

Thereafter, the jig 20 is fitted into the stent 10, and a taping process of winding a second sheet of polytetrafluoroethylene (PTFE) tape 32 on the entire outer surface of the stent 10 is performed.

Here, the second sheet of PTFE tape 32 is wound on the stent 10 only in the spiral direction of the stent 10, only in the circumferential direction of the stent 10, or in a combination of the spiral and circumferential directions of the stent 10.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50a of a lower elastic member 50, which is formed in the same shape as a portion of the jig 20, and then is fitted into a first receiving portion 51a of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50a of the lower elastic member 50 and the first receiving portion 51a of the upper elastic member 51 are deformed so as to be expanded due to the thickness of the stent 10.

Thereafter, the lower elastic member 50 and the upper elastic member 51 are fitted into a first receiving portion 60a of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills the plurality of spaces 11.

Here, pressure is uniformly transmitted, rather than being biased toward a certain point, from the first receiving portion 60a of the mold 60 and the press member 61 to the entire areas of the lower elastic member 50 and the upper elastic member 51 expanded by deformation of the first receiving portions 50a and 51a due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60a of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheet of PTFE tape 32 wound on the stent 10.

In addition, the second sheet of PTFE tape 32 wound on the stent 10, which is pressed by the lower elastic member 50 and the upper elastic member 51, is inserted into the spaces 11 in the stent 10, and is brought into close contact with and adhered to the first sheet of PTFE tape 31 wound on the jig 20.

Meanwhile, the mold 60 may be composed of at least two components coupled to each other so as to form the first receiving portion 60a therebetween.

Thereafter, the pressing operation of the press member 61 is terminated, and the lower elastic member 50 and the upper elastic member 51 are taken out of the first receiving portion 60a of the mold 60. Thereafter, the stent 10 is taken out of the first receiving portion 50a of the lower elastic member 50 and the first receiving portion 51a of the upper elastic member 51, and the jig 20 is removed from the stent 10.

Here, the press member 61 is connected to a cylinder rod of a cylinder 61a configured to be operated by hydraulic pressure or pneumatic pressure, and the cylinder 61a drives the press member 61 to press or release the upper elastic member 51.

The stent 10 having the PTFE film 30 formed thereon according to the first embodiment of the present invention is manufactured through the above-described processes, and is inserted into a narrowed or occluded lesion in a lumen in a human body to expand the lesion.

In addition, as shown in FIGS. 3 to 5 and 14 to 22, a method of manufacturing a stent 10 according to a second embodiment of the present invention, on which a PTFE film 30 is formed, includes a process of preparing a jig 20 manufactured in the same shape as the stent 10 and a taping process of winding a first sheet of polytetrafluoroethylene (PTFE) tape 31 on each of two opposite sides of the outer surface of the jig 20, i.e. each of two opposite end portions of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheet of PTFE tape 31 is wound on the jig 20 only in the spiral direction of the jig 20, only in the circumferential direction of the jig 20, or in a combination of the spiral and circumferential directions of the jig 20.

Thereafter, the jig 20 is fitted into the stent 10, and a taping process of winding a second sheet of polytetrafluoroethylene (PTFE) tape 32 on the entire outer surface of the stent 10 is performed.

Here, the second sheet of PTFE tape 32 is wound on the stent 10 only in the spiral direction of the stent 10, only in the circumferential direction of the stent 10, or in a combination of the spiral and circumferential directions of the stent 10.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50a of a lower elastic member 50, which is formed in the same shape as a portion of the jig 20, and then is fitted into a first receiving portion 51a of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50a of the lower elastic member 50 and the first receiving portion 51a of the upper elastic member 51 are deformed so as to be expanded due to the thickness of the stent 10.

Thereafter, the lower elastic member 50 and the upper elastic member 51 are fitted into a first receiving portion 60a of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills some of the plurality of spaces 11.

Here, pressure is uniformly transmitted, rather than being biased toward a certain point, from the first receiving portion 60a of the mold 60 and the press member 61 to the entire areas of the lower elastic member 50 and the upper elastic member 51 expanded by deformation of the first receiving portions 50a and 51a due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60a of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheet of PTFE tape 32 wound on the stent 10.

In addition, the second sheet of PTFE tape 32 wound on the stent 10, which is pressed by the lower elastic member 50 and the upper elastic member 51, is inserted into the spaces 11 in the stent 10, and is brought into close contact with and adhered to the first sheet of PTFE tape 31 wound on the jig 20.

In this case, the remaining portion of the second sheet of PTFE tape 32 that is not adhered to the first sheet of PTFE tape 31 is in a free state on the stent 10.

Meanwhile, the mold 60 may be composed of at least two components coupled to each other so as to form the first receiving portion 60a therebetween.

Thereafter, the pressing operation of the press member 61 is terminated, and the lower elastic member 50 and the upper elastic member 51 are taken out of the first receiving portion 60a of the mold 60. Thereafter, the stent 10 is taken out of the first receiving portion 50a of the lower elastic member 50 and the first receiving portion 51a of the upper elastic member 51, and the jig 20 is removed from the stent 10.

Here, the press member 61 is connected to a cylinder rod of a cylinder 61a configured to be operated by hydraulic pressure or pneumatic pressure, and the cylinder 61a drives the press member 61 to press or release the upper elastic member 51.

The stent 10 having the PTFE film 30 formed thereon according to the second embodiment of the present invention is manufactured through the above-described processes, and is inserted into a narrowed or occluded lesion in a lumen in a human body to expand the lesion.

In addition, as shown in FIGS. 3 to 5 and 23 to 31, a method of manufacturing a stent 10 according to a third embodiment of the present invention, on which a PTFE film 30 is formed, includes a process of preparing a jig 20 manufactured in the same shape as the stent 10 and a taping process of winding a first sheet of polytetrafluoroethylene (PTFE) tape 31 on the entire outer surface of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheet of PTFE tape 31 is wound on the jig 20 only in the spiral direction of the jig 20, only in the circumferential direction of the jig 20, or in a combination of the spiral and circumferential directions of the jig 20.

Thereafter, the jig 20 is fitted into the stent 10, and a taping process of winding a second sheet of polytetrafluoroethylene (PTFE) tape 32 on each of two opposite sides of the outer surface of the stent 10, i.e. each of two opposite end portions of the stent 10, is performed.

Here, the second sheet of PTFE tape 32 is wound on the stent 10 only in the spiral direction of the stent 10, only in the circumferential direction of the stent 10, or in a combination of the spiral and circumferential directions of the stent 10.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50a of a lower elastic member 50, which is formed in the same shape as a portion of the jig 20, and then is fitted into a first receiving portion 51a of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50a of the lower elastic member 50 and the first receiving portion 51a of the upper elastic member 51 are deformed so as to be expanded due to the thickness of the stent 10.

Thereafter, the lower elastic member 50 and the upper elastic member 51 are fitted into a first receiving portion 60a of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills some of the plurality of spaces 11.

Here, pressure is uniformly transmitted, rather than being biased toward a certain point, from the first receiving portion 60a of the mold 60 and the press member 61 to the entire areas of the lower elastic member 50 and the upper elastic member 51 expanded by deformation of the first receiving portions 50a and 51a due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60a of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheet of PTFE tape 32 wound on the stent 10.

In addition, the second sheet of PTFE tape 32 wound on the stent 10, which is pressed by the lower elastic member 50 and the upper elastic member 51, is inserted into the spaces 11 in the stent 10, and is brought into close contact with and adhered to the first sheet of PTFE tape 31 wound on the jig 20.

In this case, the remaining portion of the first sheet of PTFE tape 31 that is not adhered to the second sheet of PTFE tape 32 is in a free state on the stent 10.

Meanwhile, the mold 60 may be composed of at least two components coupled to each other so as to form the first receiving portion 60a therebetween.

Thereafter, the pressing operation of the press member 61 is terminated, and the lower elastic member 50 and the upper elastic member 51 are taken out of the first receiving portion 60a of the mold 60. Thereafter, the stent 10 is taken out of the first receiving portion 50a of the lower elastic member 50 and the first receiving portion 51a of the upper elastic member 51, and the jig 20 is removed from the stent 10.

Here, the press member 61 is connected to a cylinder rod of a cylinder 61a configured to be operated by hydraulic pressure or pneumatic pressure, and the cylinder 61a drives the press member 61 to press or release the upper elastic member 51.

The stent 10 having the PTFE film 30 formed thereon according to the third embodiment of the present invention is manufactured through the above-described processes, and is inserted into a narrowed or occluded lesion in a lumen in a human body to expand the lesion.

In addition, as shown in FIGS. 3 to 5 and 32 to 40, a method of manufacturing a stent 10 according to a fourth embodiment of the present invention, on which a PTFE film 30 is formed, includes a process of preparing a jig 20 manufactured in the same shape as the stent 10 and a taping process of winding first sheets of polytetrafluoroethylene (PTFE) tape 31 on the outer surface of the jig 20 such that the first sheets of PTFE tape 31 are disposed at predetermined intervals in the longitudinal direction of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheets of PTFE tape 31 are wound on the jig 20 only in the spiral direction of the jig 20, only in the circumferential direction of the jig 20, or in a combination of the spiral and circumferential directions of the jig 20.

In addition, the first sheets of PTFE tape 31 are wound on the outer surface of the jig 20 so as to be disposed at regular intervals or irregular intervals in the longitudinal direction of the jig 20.

In addition, the plurality of first sheets of PTFE tape 31 wound on the outer surface of the jig 20 is formed to have the same length as or different lengths from each other in the longitudinal direction thereof.

Thereafter, the jig 20 is fitted into the stent 10, and a taping process of winding a second sheet of polytetrafluoroethylene (PTFE) tape 32 on the entire outer surface of the stent 10 is performed.

Here, the second sheet of PTFE tape 32 is wound on the stent 10 only in the spiral direction of the stent 10, only in the circumferential direction of the stent 10, or in a combination of the spiral and circumferential directions of the stent 10.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50a of a lower elastic member 50, which is formed in the same shape as a portion of the jig 20, and then is fitted into a first receiving portion 51a of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50a of the lower elastic member 50 and the first receiving portion 51a of the upper elastic member 51 are deformed so as to be expanded due to the thickness of the stent 10.

Thereafter, the lower elastic member 50 and the upper elastic member 51 are fitted into a first receiving portion 60a of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills some of the plurality of spaces 11.

Here, pressure is uniformly transmitted, rather than being biased toward a certain point, from the first receiving portion 60a of the mold 60 and the press member 61 to the entire areas of the lower elastic member 50 and the upper elastic member 51 expanded by deformation of the first receiving portions 50a and 51a due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60a of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheet of PTFE tape 32 wound on the stent 10.

In addition, the second sheet of PTFE tape 32 wound on the stent 10, which is pressed by the lower elastic member 50 and the upper elastic member 51, is inserted into the spaces 11 in the stent 10, and is brought into close contact with and adhered to the first sheets of PTFE tape 31 wound on the jig 20.

In this case, the remaining portion of the second sheet of PTFE tape 32 that is not adhered to the first sheets of PTFE tape 31 is in a free state on the stent 10.

Meanwhile, the mold 60 may be composed of at least two components coupled to each other so as to form the first receiving portion 60a therebetween.

Thereafter, the pressing operation of the press member 61 is terminated, and the lower elastic member 50 and the upper elastic member 51 are taken out of the first receiving portion 60a of the mold 60. Thereafter, the stent 10 is taken out of the first receiving portion 50a of the lower elastic member 50 and the first receiving portion 51a of the upper elastic member 51, and the jig 20 is removed from the stent 10.

Here, the press member 61 is connected to a cylinder rod of a cylinder 61a configured to be operated by hydraulic pressure or pneumatic pressure, and the cylinder 61a drives the press member 61 to press or release the upper elastic member 51.

The stent 10 having the PTFE film 30 formed thereon according to the fourth embodiment of the present invention is manufactured through the above-described processes, and is inserted into a narrowed or occluded lesion in a lumen in a human body to expand the lesion.

In addition, as shown in FIGS. 3 to 5 and 41 to 49, a method of manufacturing a stent 10 according to a fifth embodiment of the present invention, on which a PTFE film 30 is formed, includes a process of preparing a jig 20 manufactured in the same shape as the stent 10 and a taping process of winding a first sheet of polytetrafluoroethylene (PTFE) tape 31 on the entire outer surface of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheet of PTFE tape 31 is wound on the jig 20 only in the spiral direction of the jig 20, only in the circumferential direction of the jig 20, or in a combination of the spiral and circumferential directions of the jig 20.

Thereafter, the jig 20 is fitted into the stent 10, and a taping process of winding second sheets of polytetrafluoroethylene (PTFE) tape 32 on the outer surface of the stent 10 such that the second sheets of PTFE tape 32 are disposed at predetermined intervals in the longitudinal direction of the stent 10 is performed.

Here, the second sheets of PTFE tape 32 are wound on the stent 10 only in the spiral direction of the stent 10, only in the circumferential direction of the stent 10, or in a combination of the spiral and circumferential directions of the stent 10.

In addition, the second sheets of PTFE tape 32 are wound on the outer surface of the stent 10 so as to be disposed at regular intervals or irregular intervals in the longitudinal direction of the stent 10.

In addition, the plurality of second sheets of PTFE tape 32 wound on the outer surface of the stent 10 is formed to have the same length as or different lengths from each other in the longitudinal direction thereof.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50*a* of a lower elastic member 50, which is formed in the same shape as a portion of the jig 20, and then is fitted into a first receiving portion

51*a* of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50*a* of the lower elastic member 50 and the first receiving portion 51*a* of the upper elastic member 51 are deformed so as to be expanded due to the thickness of the stent 10.

Thereafter, the lower elastic member 50 and the upper elastic member 51 are fitted into a first receiving portion 60*a* of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills some of the plurality of spaces 11.

Here, pressure is uniformly transmitted, rather than being biased toward a certain point, from the first receiving portion 60*a* of the mold 60 and the press member 61 to the entire areas of the lower elastic member 50 and the upper elastic member 51 expanded by deformation of the first receiving portions 50*a* and 51*a* due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60*a* of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheets of PTFE tape 32 wound on the stent 10.

In addition, the second sheets of PTFE tape 32 wound on the stent 10, which are pressed by the lower elastic member 50 and the upper elastic member 51, are inserted into the spaces 11 in the stent 10, and are brought into close contact with and adhered to the first sheet of PTFE tape 31 wound on the jig 20.

In this case, the remaining portion of the first sheet of PTFE tape 31 that is not adhered to the second sheets of PTFE tape 32 is in a free state on the stent 10.

Meanwhile, the mold 60 may be composed of at least two components coupled to each other so as to form the first receiving portion 60*a* therebetween.

Thereafter, the pressing operation of the press member 61 is terminated, and the lower elastic member 50 and the upper elastic member 51 are taken out of the first receiving portion 60*a* of the mold 60. Thereafter, the stent 10 is taken out of the first receiving portion 50*a* of the lower elastic member 50 and the first receiving portion 51*a* of the upper elastic member 51, and the jig 20 is removed from the stent 10.

Here, the press member 61 is connected to a cylinder rod of a cylinder 61*a* configured to be operated by hydraulic pressure or pneumatic pressure, and the cylinder 61*a* drives the press member 61 to press or release the upper elastic member 51.

The stent 10 having the PTFE film 30 formed thereon according to the fifth embodiment of the present invention is manufactured through the above-described processes, and is inserted into a narrowed or occluded lesion in a lumen in a human body to expand the lesion.

In addition, as shown in FIGS. 3 to 5 and 50 to 58, a method of manufacturing a stent 10 according to a sixth embodiment of the present invention, on which a PTFE film 30 is formed, includes a process of preparing a jig 20 manufactured in the same shape as the stent 10 and a taping process of winding first sheets of polytetrafluoroethylene (PTFE) tape 31 on the outer surface of the jig 20 such that the first sheets of PTFE tape 31 are disposed at predetermined intervals in the longitudinal direction of the jig 20.

Here, the stent 10 is manufactured in a manner of weaving or crossing one or more wires 12, which are made of a hyper-elastic shape memory alloy, in the form of a hollow cylindrical mesh or in the form of a mesh having a hollow cylindrical portion and at least one expanded portion having a larger diameter than the hollow cylindrical portion in accordance with the shape of a jig used for manufacture of the stent. The stent has a plurality of spaces 11 defined in the outer surface thereof.

That is, the stent 10 is formed in a hollow cylindrical shape or a shape having a hollow cylindrical portion and at least one expanded portion having a larger diameter than the hollow cylindrical portion, and the expanded portion is formed in any of various shapes in accordance with the shape of the jig used for manufacture of the stent.

In addition, the jig 20 is formed in the same shape as the stent 10 so as to be fitted into the stent 10, and is made of a metal material.

In addition, the first sheets of PTFE tape 31 are wound on the jig 20 only in the spiral direction of the jig 20, only in the circumferential direction of the jig 20, or in a combination of the spiral and circumferential directions of the jig 20.

In addition, the first sheets of PTFE tape 31 are wound on the outer surface of the jig 20 so as to be disposed at regular intervals or irregular intervals in the longitudinal direction of the jig 20.

In addition, the plurality of first sheets of PTFE tape 31 wound on the outer surface of the jig 20 is formed to have the same length as or different lengths from each other in the longitudinal direction thereof.

Thereafter, the jig 20 is fitted into the stent 10, and a taping process of winding second sheets of polytetrafluoroethylene (PTFE) tape 32 on the outer surface of the stent 10 such that the second sheets of PTFE tape 32 are disposed at predetermined intervals in the longitudinal direction of the stent 10 so as to respectively face the first sheets of polytetrafluoroethylene (PTFE) tape 31 is performed.

Here, the second sheets of PTFE tape 32 are wound on the stent 10 only in the spiral direction of the stent 10, only in the circumferential direction of the stent 10, or in a combination of the spiral and circumferential directions of the stent 10.

In addition, the second sheets of PTFE tape 32 are wound on the outer surface of the stent 10 so as to be disposed at regular intervals or irregular intervals in the longitudinal direction of the stent 10.

That is, the second sheets of PTFE tape 32 are wound on the outer surface of the stent 10 so as to be disposed at the same intervals as the first sheets of PTFE tape 31.

In addition, the plurality of second sheets of PTFE tape 32 wound on the outer surface of the stent 10 is formed to have the same length as or different lengths from each other in the longitudinal direction thereof.

Thereafter, the stent 10, with the jig 20 fitted thereinto, is put into an oven 40 to be heated so that the first and second sheets of polytetrafluoroethylene (PTFE) tape 31 and 32 become ready to be adhered to each other, and then is taken out of the oven 40.

Here, the oven 40 heats the stent 10, with the jig 20 fitted thereinto, to 300° C. or higher, and the first and second sheets of PTFE tape 31 and 32 are softened at a temperature of 300° C. or higher and become ready to be adhered to each other.

Thereafter, the jig 20 and the stent 10 heated as described above, with the first and second sheets of polytetrafluoroethylene (PTFE) tape 31 and 32 respectively wound thereon, are fitted into a first receiving portion 50a of a lower elastic member 50, which is formed in the same shape as a portion of the jig 20, and then is fitted into a first receiving portion 51a of an upper elastic member 51, which is formed in the same shape as the remaining portion of the jig 20.

Here, the lower elastic member 50 and the upper elastic member 51 are made of silicone or rubber, and are connected to each other via a hinge member.

In addition, the first receiving portion 50a of the lower elastic member 50 and the first receiving portion 51a of the upper elastic member 51 are deformed so as to be expanded due to the thickness of the stent 10.

Thereafter, the lower elastic member 50 and the upper elastic member 51 are fitted into a first receiving portion 60a of a mold 60, which is formed in the same shape as the lower elastic member 50 and the upper elastic member 51, and the upper elastic member 51 is pressed by a press member 61 so that the entire areas of the lower elastic member 50 and the upper elastic member 51 receive pressure from the mold 60 and the press member 61, whereby the first and second sheets of polytetrafluoroethylene (PTFE) tape 31 and 32 are adhered to each other to form a PTFE film 30 on the stent 10, and the PTFE film 30 fills some of the plurality of spaces 11.

Here, pressure is uniformly transmitted, rather than being biased toward a certain point, from the first receiving portion 60a of the mold 60 and the press member 61 to the entire areas of the lower elastic member 50 and the upper elastic member 51 expanded by deformation of the first receiving portions 50a and 51a due to the thickness of the stent 10.

In addition, the lower elastic member 50 and the upper elastic member 51 uniformly press the entire areas of the jig 20 and the stent 10, with the first and second sheets of PTFE tape 31 and 32 respectively wound thereon, using the pressure uniformly transmitted thereto from the first receiving portion 60a of the mold 60 and the press member 61.

In addition, while portions of the lower elastic member 50 and the upper elastic member 51, which are in close contact with the wire 12 of the stent 10, are not deformed, the remaining portions of the lower elastic member 50 and the upper elastic member 51, which are not in close contact with the wire 12 of the stent 10, are deformed to be inserted into the spaces 11 in the stent 10, and thus press the second sheets of PTFE tape 32 wound on the stent 10.

In addition, the second sheets of PTFE tape 32 wound on the stent 10, which are pressed by the lower elastic member 50 and the upper elastic member 51, are inserted into the spaces 11 in the stent 10, and are brought into close contact with and adhered to the first sheets of PTFE tape 31 wound on the jig 20.

Meanwhile, the mold 60 may be composed of at least two components coupled to each other so as to form the first receiving portion 60a therebetween.

Thereafter, the pressing operation of the press member 61 is terminated, and the lower elastic member 50 and the upper elastic member 51 are taken out of the first receiving portion 60a of the mold 60. Thereafter, the stent 10 is taken out of the first receiving portion 50a of the lower elastic member 50 and the first receiving portion 51a of the upper elastic member 51, and the jig 20 is removed from the stent 10.

Here, the press member 61 is connected to a cylinder rod of a cylinder 61a configured to be operated by hydraulic pressure or pneumatic pressure, and the cylinder 61a drives the press member 61 to press or release the upper elastic member 51.

The stent 10 having the PTFE film 30 formed thereon according to the sixth embodiment of the present invention is manufactured through the above-described processes, and is inserted into a narrowed or occluded lesion in a lumen in a human body to expand the lesion.

Figure 59:
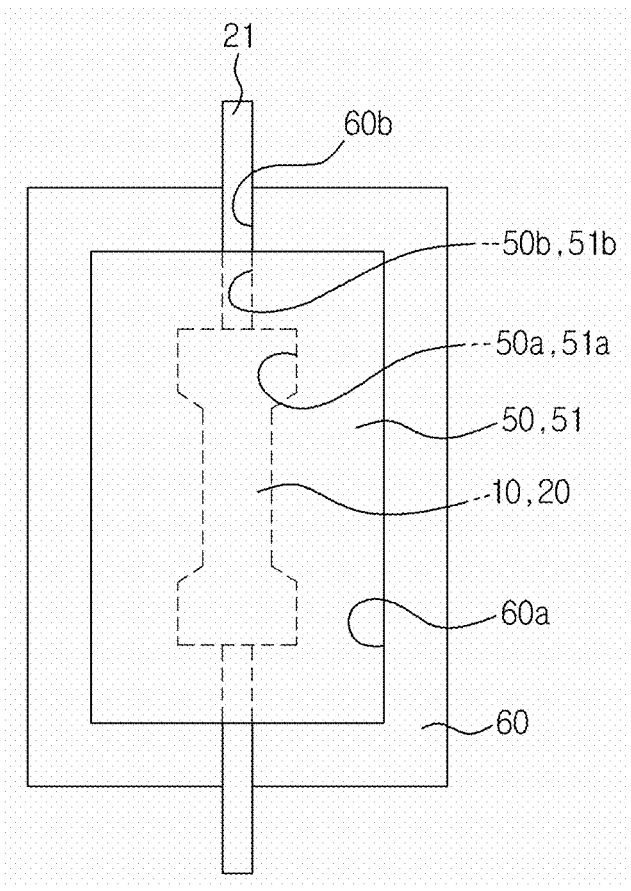
FIG. 59 is a plan view of upper and lower elastic members and a mold according to another embodiment as an alternative to the first, second, third, fourth, fifth, and sixth embodiments of the present invention.

In addition, as shown in FIG. 59, a jig 20 according to another embodiment as an alternative to the first, second, third, fourth, fifth, and sixth embodiments of the present invention has a knob 21 protruding from an outer surface thereof.

Here, the knob 21 protrudes from one side or each of two opposite sides of the outer surface of the jig 20.

Therefore, the jig 20 and the stent 10 are taken out of the oven 40 using the knob 21, rather than using the heated first and second sheets of polytetrafluoroethylene (PTFE) tape 31 and 32.

In addition, the lower elastic member 50 and the upper elastic member 51 have second receiving portions 50b and 51b respectively formed in the outer surfaces thereof to allow the knob 21 to be fitted thereinto. The second receiving portions 50b and 51b are respectively connected to the first receiving portions 50a and 51a.

In addition, the mold 60 has a second receiving portion 60b formed in the outer surface thereof to allow the knob 21 to be fitted thereinto. The second receiving portion 60b is connected to the first receiving portion 60a.

Therefore, the lower elastic member 50 and the upper elastic member 51 are taken out of the first receiving portion 60a of the mold 60 using the knob 21, and the stent 10 is taken out of the first receiving portion 50a of the lower elastic member 50 and the first receiving portion 51a of the upper elastic member 51 using the knob 21.

Figure 60:
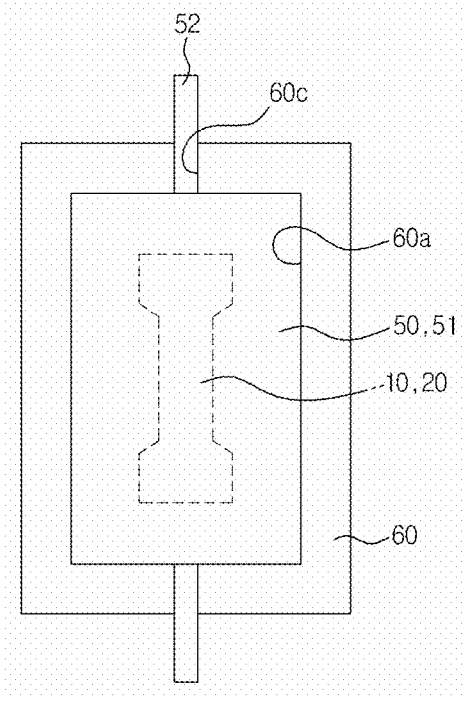
FIG. 60 is a plan view of upper and lower elastic members and a mold according to still another embodiment as an alternative to the first, second, third, fourth, fifth, and sixth embodiments of the present invention.

In addition, as shown in FIG. 60, each of a lower elastic member 50 and an upper elastic member 51 according to still another embodiment as an alternative to the first, second, third, fourth, fifth, and sixth embodiments of the present invention has a knob 52 protruding from an outer surface thereof.

Here, the knob 52 protrudes from one side or each of two opposite sides of the outer surface of each of the lower elastic member 50 and the upper elastic member 51.

In addition, the mold 60 has a third receiving portion 60c formed in the outer surface thereof to allow the knob 52 to be fitted thereinto. The third receiving portion 60c is connected to the first receiving portion 60a.

Therefore, the lower elastic member 50 and the upper elastic member 51 are taken out of the first receiving portion 60a of the mold 60 using the knob 52.

Figure 61:
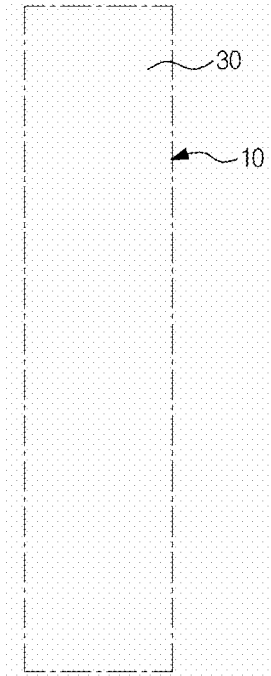
FIG. 61 is a front view of a stent having a PTFE film formed thereon according to yet still another embodiment as an alternative to the first, second, third, fourth, fifth, and sixth embodiments of the present invention.

In addition, as shown in FIG. 61, a stent 10 having a PTFE film 30 formed thereon according to yet still another embodiment as an alternative to the first, second, third, fourth, fifth, and sixth embodiments of the present invention may be formed in a hollow cylindrical shape that does not have an expanded portion having a larger diameter than the stent 10.

Although the specific preferred embodiments of the present invention have been illustrated and described above, the present invention is not limited to the embodiments, and various changes and modifications may be made by those skilled in the art without departing from the spirit of the present invention.

| *Description of Reference Numerals* | |
|---|---|
| 10: stent | 11: space |
| 20: jig | 21: knob |
| 30: PTFE film | 31: first sheet of PTFE tape |
| 32: second sheet of PTFE tape | 40: oven |
| 50: lower elastic member | 50a: first receiving portion |
| 50b: second receiving portion | 51: upper elastic member |
| 51a: first receiving portion | 51b: second receiving portion |
| 52: knob | 60: mold |
| 60a: first receiving portion | 60b: second receiving portion |
| 60c: third receiving portion | 61: press member |
| 61a: cylinder | |

The invention claimed is:

1. A method of forming a PTFE film on a stent, the method comprising:

performing a taping process of winding a first sheet of polytetrafluoroethylene (PTFE) tape (31) on an entire outer surface of a jig (20) being manufactured in a same shape as a stent (10) having a plurality of spaces (11);

fitting the jig (20) into a stent (10) and performing a taping process of winding a second sheet of polytetrafluoroethylene (PTFE) tape (32) on an entire outer surface of the stent (10);

putting the stent (10), with the jig (20) fitted thereinto, into an oven (40) to heat the jig (20) and the stent (10) so that the first and second sheets of polytetrafluoroethylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50a) of a lower elastic member (50), the first receiving portion (50a) being formed in a same shape as a portion of the jig (20), and a first receiving portion (51a) of an upper elastic member (51), the first receiving portion (51a) being formed in a same shape as a remaining portion of the jig (20);

fitting the lower elastic member (50) and the upper elastic member (51) into a first receiving portion (60a) of a mold (60), the first receiving portion (60a) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills a plurality of spaces (11); and taking the lower elastic member (50) and the upper elastic member (51) out of the first receiving portion (60a) of the mold (60), with pressure transmitted from the press member (61) released, taking the stent (10) out of the first receiving portion (50a) of the lower elastic member (50) and the first receiving portion (51a) of the upper elastic member (51), and removing the jig (20) from the stent (10).

2. The method according to claim 1, wherein the lower elastic member (50) and the upper elastic member (51) are made of silicone or rubber.

3. The method according to claim 1, wherein the press member (61) presses or releases the upper elastic member (51) using a cylinder (61a) configured to be operated by hydraulic pressure or pneumatic pressure.

4. The method according to claim 1, wherein the jig (20) has a knob (21) formed on an outer surface thereof, wherein the lower elastic member (50) and the upper elastic member (51) have second receiving portions (50b and 51b) respectively formed in outer surfaces thereof to allow the knob (21) to be fitted thereinto, the second receiving portions (50b and 51b) being respectively connected to the first receiving portions (50a and 51a), and wherein the mold (60) has a second receiving portion (60b) formed in an outer surface thereof to allow the knob (21) to be fitted thereinto, the second receiving portion (60b) being connected to the first receiving portion (60a).

5. The method according to claim 1, wherein each of the lower elastic member (50) and the upper elastic member (51) has a knob (52) formed on an outer surface thereof, and wherein the mold (60) has a third receiving portion (60c) formed in an outer surface thereof to allow the knob (52) to be fitted thereinto, the third receiving portion (60c) being connected to the first receiving portion (60a).

6. A stent manufactured through the method of forming a PTFE film on a stent described in claim 1.

7. A method of forming a PTFE film on a stent, the method comprising:

performing a taping process of winding a first sheet of polytetrafluoroethylene (PTFE) tape (31) on each of two opposite sides of an outer surface of a jig (20) being manufactured in a same shape as a stent (10) having a plurality of spaces (11);

fitting the jig (20) into a stent (10) and performing a taping process of winding a second sheet of polytetrafluoroethylene (PTFE) tape (32) on an entire outer surface of the stent (10);

putting the stent (10), with the jig (20) fitted thereinto, into an oven (40) to heat the jig (20) and the stent (10) so that the first and second sheets of polytetrafluoroethylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50a) of a lower elastic member (50), the first receiving portion (50a) being formed in a same shape as a portion of the jig (20), and a first receiving portion (51a) of an upper elastic member (51), the first receiving portion (51a) being formed in a same shape as a remaining portion of the jig (20);

fitting the lower elastic member (50) and the upper elastic member (51) into a first receiving portion (60a) of a mold (60), the first receiving portion (60a) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills some of a plurality of spaces (11); and taking the lower elastic member (50) and the upper elastic member (51) out of the first receiving portion (60a) of the mold (60), with pressure transmitted from the press member (61) released, taking the stent (10) out of the first receiving portion (50a) of the lower elastic member (50) and the first receiving portion (51a) of the upper elastic member (51), and removing the jig (20) from the stent (10).

8. The method according to claim 7, wherein the lower elastic member (50) and the upper elastic member (51) are made of silicone or rubber.

9. The method according to claim 7, wherein the press member (61) presses or releases the upper elastic member (51) using a cylinder (61a) configured to be operated by hydraulic pressure or pneumatic pressure.

10. The method according to claim 7, wherein the jig (20) has a knob (21) formed on an outer surface thereof, wherein the lower elastic member (50) and the upper elastic member (51) have second receiving portions (50b and 51b) respectively formed in outer surfaces thereof to allow the knob (21) to be fitted thereinto, the second receiving portions (50b and 51b) being respectively connected to the first receiving portions (50a and 51a), and wherein the mold (60) has a second receiving portion (60b) formed in an outer surface thereof to allow the knob (21) to be fitted thereinto, the second receiving portion (60b) being connected to the first receiving portion (60a).

11. The method according to claim 7, wherein each of the lower elastic member (50) and the upper elastic member (51) has a knob (52) formed on an outer surface thereof, and wherein the mold (60) has a third receiving portion (60c) formed in an outer surface thereof to allow the knob (52) to be fitted thereinto, the third receiving portion (60c) being connected to the first receiving portion (60a).

12. A stent manufactured through the method of forming a PTFE film on a stent described in claim 7.

13. A method of forming a PTFE film on a stent, the method comprising:

performing a taping process of winding a first sheet of polytetrafluoroethylene (PTFE) tape (31) on an entire outer surface of a jig (20) being manufactured in a same shape as a stent (10) having a plurality of spaces (11);

fitting the jig (20) into a stent (10) and performing a taping process of winding a second sheet of polytetrafluoroethylene (PTFE) tape (32) on each of two opposite sides of an outer surface of the stent (10);

putting the stent (10), with the jig (20) fitted thereinto, into an oven (40) to heat the jig (20) and the stent (10) so that the first and second sheets of polytetrafluoroethylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50a) of a lower elastic member (50), the first receiving portion (50a) being formed in a same shape as a portion of the jig (20), and a first receiving portion (51a) of an upper elastic member (51), the first receiving portion (51*a*) being formed in a same shape as a remaining portion of the jig (20);

fitting the lower elastic member (50) and the upper elastic member (51) into a first receiving portion (60*a*) of a mold (60), the first receiving portion (60*a*) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills some of a plurality of spaces (11); and taking the lower elastic member (50) and the upper elastic member (51) out of the first receiving portion (60*a*) of the mold (60), with pressure transmitted from the press member (61) released, taking the stent (10) out of the first receiving portion (50*a*) of the lower elastic member (50) and the first receiving portion (51*a*) of the upper elastic member (51), and removing the jig (20) from the stent (10).

14. The method according to claim 13, wherein the lower elastic member (50) and the upper elastic member (51) are made of silicone or rubber.

15. The method according to claim 13, wherein the press member (61) presses or releases the upper elastic member (51) using a cylinder (61*a*) configured to be operated by hydraulic pressure or pneumatic pressure.

16. The method according to claim 13, wherein the jig (20) has a knob (21) formed on an outer surface thereof, wherein the lower elastic member (50) and the upper elastic member (51) have second receiving portions (50*b* and 51*b*) respectively formed in outer surfaces thereof to allow the knob (21) to be fitted thereinto, the second receiving portions (50*b* and 51*b*) being respectively connected to the first receiving portions (50*a* and 51*a*), and wherein the mold (60) has a second receiving portion (60*b*) formed in an outer surface thereof to allow the knob (21) to be fitted thereinto, the second receiving portion (60*b*) being connected to the first receiving portion (60*a*).

17. The method according to claim 13, wherein each of the lower elastic member (50) and the upper elastic member (51) has a knob (52) formed on an outer surface thereof, and wherein the mold (60) has a third receiving portion (60*c*) formed in an outer surface thereof to allow the knob (52) to be fitted thereinto, the third receiving portion (60*c*) being connected to the first receiving portion (60*a*).

18. A stent manufactured through the method of forming a PTFE film on a stent described in claim 13.

19. A method of forming a PTFE film on a stent, the method comprising:

performing a taping process of winding first sheets of polytetrafluoroethylene (PTFE) tape (31) on an outer surface of a jig (20) being manufactured in a same shape as a stent (10) having a plurality of spaces (11) so as to be disposed at predetermined intervals in a longitudinal direction of the jig (20);

fitting the jig (20) into a stent (10) and performing a taping process of winding a second sheet of polytetrafluoro-ethylene (PTFE) tape (32) on an entire outer surface of the stent (10);

putting the stent (10), with the jig (20) fitted thereinto, into an oven (40) to heat the jig (20) and the stent (10) so that the first and second sheets of polytetrafluoroeth-ylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50*a*) of a lower elastic member (50), the first receiving portion (50*a*) being formed in a same shape as a portion of the jig (20), and a first receiving portion (51*a*) of an upper elastic member (51), the first receiving portion (51*a*) being formed in a same shape as a remaining portion of the jig (20);

fitting the lower elastic member (50) and the upper elastic member (51) into a first receiving portion (60*a*) of a mold (60), the first receiving portion (60*a*) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills some of a plurality of spaces (11); and taking the lower elastic member (50) and the upper elastic member (51) out of the first receiving portion (60*a*) of the mold (60), with pressure transmitted from the press member (61) released, taking the stent (10) out of the first receiving portion (50*a*) of the lower elastic mem-ber (50) and the first receiving portion (51*a*) of the upper elastic member (51), and removing the jig (20) from the stent (10).

20. The method according to claim 19, wherein the lower elastic member (50) and the upper elastic member (51) are made of silicone or rubber.

21. The method according to claim 19, wherein the press member (61) presses or releases the upper elastic member (51) using a cylinder (61*a*) configured to be operated by hydraulic pressure or pneumatic pressure.

22. The method according to claim 19, wherein the jig (20) has a knob (21) formed on an outer surface thereof, wherein the lower elastic member (50) and the upper elastic member (51) have second receiving portions (50*b* and 51*b*) respectively formed in outer surfaces thereof to allow the knob (21) to be fitted thereinto, the second receiving portions (50*b* and 51*b*) being respec-tively connected to the first receiving portions (50*a* and 51*a*), and wherein the mold (60) has a second receiving portion (60*b*) formed in an outer surface thereof to allow the knob (21) to be fitted thereinto, the second receiving portion (60*b*) being connected to the first receiving portion (60*a*).

23. The method according to claim 19, wherein each of the lower elastic member (50) and the upper elastic member (51) has a knob (52) formed on an outer surface thereof, and wherein the mold (60) has a third receiving portion (60*c*) formed in an outer surface thereof to allow the knob (52) to be fitted thereinto, the third receiving portion (60*c*) being connected to the first receiving portion (60*a*).

24. A stent manufactured through the method of forming a PTFE film on a stent described in claim 19.

25. A method of forming a PTFE film on a stent, the method comprising:

performing a taping process of winding a first sheet of polytetrafluoroethylene (PTFE) tape (31) on an entire outer surface of a jig (20) being manufactured in a same shape as a stent (10) having a plurality of spaces (11);

fitting the jig (20) into a stent (10) and performing a taping process of winding second sheets of polytetrafluoroethylene (PTFE) tape (32) on an outer surface of the stent (10) so as to be disposed at predetermined intervals in a longitudinal direction of the stent (10);

putting the stent (10), with the jig (20) fitted thereinto, into an oven (40) to heat the jig (20) and the stent (10) so that the first and second sheets of polytetrafluoroethylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50a) of a lower elastic member (50), the first receiving portion (50a) being formed in a same shape as a portion of the jig (20), and a first receiving portion (51a) of an upper elastic member (51), the first receiving portion (51a) being formed in a same shape as a remaining portion of the jig (20);

fitting the lower elastic member (50) and the upper elastic member (51) into a first receiving portion (60a) of a mold (60), the first receiving portion (60a) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills some of a plurality of spaces (11); and taking the lower elastic member (50) and the upper elastic member (51) out of the first receiving portion (60a) of the mold (60), with pressure transmitted from the press member (61) released, taking the stent (10) out of the first receiving portion (50a) of the lower elastic member (50) and the first receiving portion (51a) of the upper elastic member (51), and removing the jig (20) from the stent (10).

26. The method according to claim 25, wherein the lower elastic member (50) and the upper elastic member (51) are made of silicone or rubber.

27. The method according to claim 25, wherein the press member (61) presses or releases the upper elastic member (51) using a cylinder (61a) configured to be operated by hydraulic pressure or pneumatic pressure.

28. The method according to claim 25, wherein the jig (20) has a knob (21) formed on an outer surface thereof, wherein the lower elastic member (50) and the upper elastic member (51) have second receiving portions (50b and 51b) respectively formed in outer surfaces thereof to allow the knob (21) to be fitted thereinto, the second receiving portions (50b and 51b) being respectively connected to the first receiving portions (50a and 51a), and wherein the mold (60) has a second receiving portion (60b) formed in an outer surface thereof to allow the knob (21) to be fitted thereinto, the second receiving portion (60b) being connected to the first receiving portion (60a).

29. The method according to claim 25, wherein each of the lower elastic member (50) and the upper elastic member (51) has a knob (52) formed on an outer surface thereof, and wherein the mold (60) has a third receiving portion (60c) formed in an outer surface thereof to allow the knob (52) to be fitted thereinto, the third receiving portion (60c) being connected to the first receiving portion (60a).

30. A stent manufactured through the method of forming a PTFE film on a stent described in claim 25.

31. A method of forming a PTFE film on a stent, the method comprising:

performing a taping process of winding first sheets of polytetrafluoroethylene (PTFE) tape (31) on an outer surface of a jig (20) being manufactured in a same shape as a stent (10) having a plurality of spaces (11) so as to be disposed at predetermined intervals in a longitudinal direction of the jig (20);

fitting the jig (20) into a stent (10) and performing a taping process of winding second sheets of polytetrafluoroethylene (PTFE) tape (32) on an outer surface of the stent (10) so as to be disposed at predetermined intervals in a longitudinal direction of the stent (10) and to respectively face the first sheets of polytetrafluoroethylene (PTFE) tape (31);

putting the stent (10), with the jig (20) fitted thereinto, into an oven (40) to heat the jig (20) and the stent (10) so that the first and second sheets of polytetrafluoroethylene (PTFE) tape (31 and 32) become ready to be adhered to each other and taking the jig (20) and the stent (10) out of the oven (40);

fitting the heated jig (20) and the heated stent (10), with the first and second sheets of polytetrafluoroethylene (PTFE) tape (31 and 32) respectively wound thereon, into a first receiving portion (50a) of a lower elastic member (50), the first receiving portion (50a) being formed in a same shape as a portion of the jig (20), and a first receiving portion (51a) of an upper elastic member (51), the first receiving portion (51a) being formed in a same shape as a remaining portion of the jig (20);

fitting the lower elastic member (50) and the upper elastic member (51) into a first receiving portion (60a) of a mold (60), the first receiving portion (60a) being formed in a same shape as the lower elastic member (50) and the upper elastic member (51), and pressing the upper elastic member (51) using a press member (61) to transmit pressure from the mold (60) and the press member (61) to entire areas of the lower elastic member (50) and the upper elastic member (51) so that the first and second sheets of polytetrafluoroethylene (PTFE) tape (31 and 32) are adhered to each other to form a PTFE film (30) on the stent (10) and the PTFE film (30) fills some of a plurality of spaces (11); and taking the lower elastic member (50) and the upper elastic member (51) out of the first receiving portion (60a) of the mold (60), with pressure transmitted from the press member (61) released, taking the stent (10) out of the first receiving portion (50a) of the lower elastic member (50) and the first receiving portion (51a) of the upper elastic member (51), and removing the jig (20) from the stent (10).

32. The method according to claim 31, wherein the lower elastic member (50) and the upper elastic member (51) are made of silicone or rubber.

33. The method according to claim 31, wherein the press member (61) presses or releases the upper elastic member (51) using a cylinder (61*a*) configured to be operated by hydraulic pressure or pneumatic pressure.

34. The method according to claim 31, wherein the jig (20) has a knob (21) formed on an outer surface thereof, wherein the lower elastic member (50) and the upper elastic member (51) have second receiving portions (50*b* and 51*b*) respectively formed in outer surfaces thereof to allow the knob (21) to be fitted thereinto, the second receiving portions (50*b* and 51*b*) being respectively connected to the first receiving portions (50*a* and 51*a*), and wherein the mold (60) has a second receiving portion (60*b*) formed in an outer surface thereof to allow the knob (21) to be fitted thereinto, the second receiving portion (60*b*) being connected to the first receiving portion (60*a*).

35. The method according to claim 31, wherein each of the lower elastic member (50) and the upper elastic member (51) has a knob (52) formed on an outer surface thereof, and wherein the mold (60) has a third receiving portion (60*c*) formed in an outer surface thereof to allow the knob (52) to be fitted thereinto, the third receiving portion (60*c*) being connected to the first receiving portion (60*a*).

36. A stent manufactured through the method of forming a PTFE film on a stent described in claim 31.

\* \* \* \* \*